United States Patent [19]

Kupfer et al.

[11] Patent Number: 5,287,273

[45] Date of Patent: Feb. 15, 1994

[54] FUNCTIONAL ORGAN IMAGES

[75] Inventors: Sherman Kupfer, New York; Peter Stritzke, White Plains, both of N.Y.

[73] Assignee: Mount Sinai School of Medicine, New York, N.Y.

[21] Appl. No.: 498,820

[22] Filed: Mar. 23, 1990

Related U.S. Application Data

[63] Continuation-in-part of Ser. No. 494,121, Mar. 15, 1990.

[51] Int. Cl.$^5$ .............................................. G06F 15/42
[52] U.S. Cl. .............................. 364/413.07; 128/653.4; 250/303
[58] Field of Search ....................... 364/413.07, 413.01, 364/413.02, 413.06, 413.09, 413.11; 128/660.01, 660.02, 660.04, 660.06, 632, 653.1, 653.2, 653.3, 653.4; 250/302, 303

[56] References Cited

PUBLICATIONS

Colin, et al "Etude experimentale du renogramme"; Arch Kreisllauff., 16:289-306 (1985).
Bassingthwaighte, "Circulatory transport and the convolution integral", Mayo. Clin. Proc. 42:137-154.
Stritzke, et al., "Non invasive assessment of absolute renal blood flow (RBF) by temporal deconvolution using orthogonal poly." J. Nucl. Med. 29:862-863.
Alazraki et al, "Reliability of Radionuclide Angiography and Renography to Detect Varying Degrees of Impaired Renal Artery Flow", In: Bischof-Delaloy et al.
Kuruc, et al., "An Improved Deconvoluion Technique for the Calculation of Renal Retention Functions", Computer and Biomedical Research, 15:46-56 (1982).
Hunt, "The Inverse Problem of Radiography", Mathematical Biosciences, 8:161-179 (1970).
Wu, et al., "Tc-99m HIDA Dosimetry in Patients with Various Hepatic Disorders", J. Nucl. Med., 25:905-912 (1984).
Siegel, et al., "The Buildup Factor: Effect of Scatter on Absolute Volume Determination", J. Nucl. Med., 26:390-394 (1985).
Stritzke et al., "Performance of Quantitative Functional Imaging Using Optimal Two-Dimensional Restoration and Temporal Deconvolution of Dynamic Scintigraphic Studies", in: Computer Assisted Radiography, Springer-Verlag, pp. 697-702 (1987).
Van Stekelenburg, et al., "A Three-compartment Model for the Transport and Distribution of Hippuran", Phys. Med. Biol., 21:74-84 (1976).
Szabo, et al., "Model identification and estimation of organ-function parameters using radioactive tracers and the impulse-response function", Eur. J. Nucl. Med., 11:265-274 (1985).

(List continued on next page.)

*Primary Examiner*—Gail O. Hayes
*Attorney, Agent, or Firm*—Brumbaugh, Graves, Donohue & Raymond

[57] ABSTRACT

A noninvasive method of determining function of a target organ using a pre-calibrated imaging system is described. The method contains the steps of introducing an indicator/tracer bolus into the subject's circulatory system and thereafter monitoring simultaneously the responses recorded from the heart/great vessels, and from the target organ. The absolute activity per unit volume of blood withdrawn at a known time(s) is measured, and the observed data from the heart or great vessels is converted into absolute units. These data serve as B(t), the input function. Precalibration of the detector/measuring system allows the observed dynamic indicator/tracer data recorded from the target organ to be expressed in units of absolute activity. These data serve as A(t). A(t) and B(t) are deconvolved in order to obtain the linear response function (LRF, h(t)) for an image element. A preferred method of deconvolution, the DOP method is introduced. Functional images of the target organ's LRF are created.

9 Claims, 13 Drawing Sheets

ORIGINAL    LRF

ORIGINAL    LRF

OTHER PUBLICATIONS

King, et al., "Digital Restoration of Indium-111 and Iodine-123 SPECT Images with Optimized Metz Filters", J. Nucl. Med., 27:1327-1336 (1986).

Van Huffel, et al., "Reliable and efficient deconvolution technique based on total linear least squares for calculating the renal retention function", Med. & Biol. Eng. & Comput., 25:26-33, (1987).

Montz et al., "Functional Imaging of Thyroidal $^{123}$I-Clearance", NucCompact, 13:176-178 (1982).

Twomy, "The Application of Numerical Filtering to the Solution of Integral Equations Encountered in Indirect Sensing Measurements", J. of the Franklin Institute, 279:95-109 (1965).

Phillips, "A Technique for the Numerical Solution of Certain Integral Equations of the First Kind", J. Assoc. Comp. Mach., 9:84-97 (1962).

Valentinuzzi, et al., "Discrete Deconvolution", Medical and Biological Engineering, 13:123-125 (1975).

Gremmel, et al., "Auswertung von Isotopennephrogrammen durch die Entfaltungsmethode", Nucl.-Med., 18:46-51 (1979).

Kenny, et al., "Deconvolution analysis of the scintillation camera renogram", B. J. of Radiology, 48:481-486 (1975).

Fleming, et al., "A Technique for the Deconvolution of the Renogram", Phys. Med. Biol., 19:546-549 (1974).

King et al., "Use of a nonstationary temporal Wiener filter in nuclear medicient", Eur. J. Nucl. Med., 10:458-461 (1985).

Knesaurek, et al., "Comparison of three deconvolution techniques in renography", Eur. J. Nucl. Med., 9:254-256 (1984).

Van Stekelenburg, "Hippuran Transit Times in the Kidney: a New Approach", Phys. Med. Biol., 23:291-301 (1978).

Diffey, et al., "the $^{99m}$Tc-$DT$PA Dynamic Renal Scan With Deconvolution Analysis", J. Nucl. Med., 17:352-355 (1976).

Keller, et al., "Direct Determination of the Attenuation Coefficient for Radionuclide Volume Measurements", J. Nucl. Med., 28:102-107 (1987).

Nimmon, et al., "Practical Application of Deconvolution Techniques to Dynamic Studies", IAEA, pp. 367 $\propto$ 388 (1981).

Zierler, "Theoretical Basis of Indicator-Dilution Methods For Measuring Flow and Volume", Circ. Research, 10:393-407 (1962).

Chackett, "The Application of Transform Methods to Hippuran Renograms", Phys. Med. Biol., 23:1199-1202 (1978).

Kaplan, et al., "The Inverse Problem of Radioisotope Diagnosis: A Computational Method for Determining the Location and Size of Tumors", Mathematical Biosciences, 5:39-55 (1969).

Kuruc, et al., "An Improved deconvolution technique for improvement after suboptimal bolus injection", Radiol., 148:233-238 (1983).

Bacharach, et al., "Optimum Fourier filtering of cardiac data: a minimum-error method", J. Nucl. Med., 24:1176-1184 (1983).

Ham, et al., "Radionuclide quantitation of left-to-right cardiac shunts using deconvolution analysis: Concise communication", J. Nucl. Med., 22:688-692 (1981).

Alderson, et al., "Deconvolution Analysis in Radionuclide Quantitation of Left-to-Right Cardiac Shunts", J. Nucl. Med., 20:502-506 (1979).

Knop, et al., "Deconvolution Analysis of $^{99m}$Te-Methylene Diphosphonate Kinetics in Metabolic Bone Disease", Eur. J. Nucl. Med., 6:63-67 (1981).

Knop, et al., "Biokinetics of Bone Tracers by Means of Deconvolution Analysis—Comparison of $^{99m}$TcMDP, $^{99m}$TcDPD and $^{99m}$Tc EHDP", Nucl.-Med., 21:144-145 (1982).

Stritzke, et al., "Funktionsszinttigraphie: Eine einheitliche Methode zur Quantifizierung von Stoffwechsel und Funktion in Organen", Nucl.-Med., 24:211-221 (1985). (and accompanying English translation).

Meier, et al., "On the Theory of the Indicator-Dilution Method for Measurement of Blood Flow and Volume", J. App. Phys., 6:731-744 (1954).

Gambhir, et al., "Simple Noninvasive Quantification Method for Measuring Myocardial Glucose Utilization in Humans Employing Positron Emission Tomography and Fluorine-18 Deoxyglucose", J. Nucl. Med., 30:359-366 (1989).

Szabo, et al., "Effects of statistical noise and digital filtering on the parameters calculated from the impulse response function", Eur. J. Nucl. Med., 13:148-154 (1987).

Peters, et al., "Non-Invasive Measurement of Renal (List continued on next page.)

OTHER PUBLICATIONS

Blood Flow (RFB) With DTPA", J. Nucl. Med., No. 373, 28 (4):646 (1987).

Mullani, et al., "First-Pass Measurements of Regional Blood Flow with External Detectors", J. Nucl. Med., 24:577-581 (1983).

Lear, et al., "Quantitative Measurement of Renal Perfusion Following Transplant Surgery", J. Nucl. Med., 29:1656-1661 (1988).

Russell, "Estimation of glomerular filtration rate using $^{99m}$Tc-DTPA and the gamma camera", Eur. J. Nucl. Med., 12:548-552 (1987).

Szabo, et al., "Parametrische Darstellung der Nierenfunktion mit $^{99m}$TC-Merkaptoazetyltriglyyzin (MAG$_3$)", Nucl.-Med., 28:73-83 (1989).

Mullani, et al., "Myocardial Perfusion with Rubidinum-82. I. Measurement of Extraction Fraction and Flow with External Detectors", J. Nucl. Med., 24:898-906 (1983).

Nally et al., "Captopril Challenge with Radionuclide Assessment in Two-Kidney and One-Kidney Goldblatt Hypertension", Contr. Nephrol., 56:104-110 (1987).

Tauxe and Duborsky, in: Nuclear Medicine in Clinical Urology and Nephrology, "Three Approaches to Computer Assisted Function Studies", Appleton—Century Crafts, Norwalk, Connecticut, pp. 175-189.

Shipley and Clark, in "Tracer Methods For In Vivo Kinetics" Academic Press, pp. 197-208 (1972).

Chinard et al., "Relative Renal Excretion Patterns of Sodium Ion, Chloride Ion, Urea, Water, Water and Glomerular Substances", Am. J. Physiol., 182:247-250 (1955).

Eigler et al., "Digital Angiographic Impulse Response Analysis of Regional Miocardial Perfusion: Linearity, Reproducibility, Accuracy and Comparison With Conventional Indicator Dilution Curve Parameters in Phantom and Canine Models", Circ. Res., 64:853-866 (1989).

Peters et al., "Noninvasive Measurement of Renal Blood Flow Using DTPA", Contr. Nephrol., 56:26-30 (1987).

Alazraki et al., "Reliability of Radionuclide Angrography and Renography to Detect Varying Degrees of Impaired Renal Artery Flow", In: Bischof-Delaloye et al. eds, Radionuclides in Nephrology, Karger, New York (1987) pp. 82-86.

Ford et al., "The Radionuclide Renogram as a Predictor of Relative Renal Blood Flow", Radiology, 149:819-821 (1983).

Ash et al., "Quantitative Assessment of Blood Flow in Paediatric Recipients of Renal Transplants", J. Nuc. Med., 29:791-792 (1988).

ORIGINAL IMAGES

.92 NIH    1.4    1.8    2.1

LINEAR RESPONSE

| .5 MIN | 1.6 | 4.8 | 6.9 |
| 9.1 | 11.2 | 13.3 | 16.5 |

FIG. 11

FUNCTIONAL ORGAN IMAGES

The present application is a continuation-in-part of U.S. patent application Ser. No. 07/494,121 filed Mar. 15, 1990, pending which is herein incorporated by reference.

BACKGROUND OF THE INVENTION

The prior art teaches extracting information from images by deconvolution by the transformation of the desired quantity (or image) by Fourier transform and subsequent arithmetic operations. Fourier transform enables the change of an image from the spatial domain to the frequency domain, while the inverse Fourier transform enables transformation from the frequency domain to the spatial domain. In the frequency domain, the computation of deconvolution with another function also in the same frequency domain requires a simple arithmetic operation, whereas in the spatial domain the deconvolution operation requires multiple steps. The added required steps in the spatial domain render deconvolution highly inefficient compared to deconvolution in the frequency domain, i.e. the same operation can be performed in the frequency domain more efficiently. This is why a tool that allows minimal operations to compute deconvolution is beneficial whenever a large number of images having multiple pixels need to be processed to extract information contained therein.

Furthermore some images, particularly those obtained from medical images, contain high amounts of noise that may render some Fourier based and other deconvolution methods ineffective. The present application describes a method that is an improvement of a medical imaging method utilizing a deconvolution method that is highly tolerant of noise contained in images. The deconvolution method provides a technique of extracting quantitative information on organ function from existing data. Methods previously in use could not provide this information except by invasive methods which expose patients to an unacceptable degree of risk.

The present invention relates to noninvasive diagnostic procedures for producing functional images from static, non-functional images. The new images are useful in determining organ activity, or linear response. The invention utilizes an array processor for the process of deconvolution to obtain the new images.

Much previous work has been done using dynamic scintigraphy to determine organ function. Such work required direct, invasive, sampling of organ efflux to measure the changing concentration of an injected indicator over time. See e.g. Chinard and Enns, "Relative Renal Excretion Patterns of Sodium Ion, Chloride Ion, Urea, Water, and Glomerular Substances", Am. J. Physiol. (1955) 182:247-250.

The formulations used in prior invasive techniques have established the mathematics involved in organ function analysis by indicator-dilution methodology. See e.g. Meier and Zeirler, "On the Theory of Indicator Dilution Method for Measurement of Blood Flow and Volume", J. App. Physiol. (1954) 6:731-744.

Methodology to reliably determine the absolute perfusion rate of an organ by a noninvasive technique, previously unavailable, is clinically important in certain diseases, organ transplantation and determination of the effects of various pharmaceutical agents. Such methodology can be used to establish diagnoses and monitor disease progression as well as response to therapy. In the past, invasive techniques with microspheres or contrast media have been used experimentally to measure flow per unit volume or weight of the organ. See e.g. Eigler et al., "Digital Angiographic Impulse Response Analysis of Regional Myocardial Perfusion: Linearity, Reproducibility, Accuracy, and Comparison With Conventional Indicator Dilution Curve Parameters in Phantom and Canine Models", Circ. Res. (1989) 64:853-866.

Previous work with dynamic scintigraphic methods, which have the virtue of being noninvasive, has provided information from which only comparative spatial and temporal evaluations could be made, i.e., one region of an organ compared to another region, one kidney compared to the other. Peters et al., "Noninvasive Measurement of Renal Blood Flow using DTPA. In: Bischof-Delaloye A, and Blaufox MD, eds., Radionuclides in Nephrology, Karger, New York (1987), pp.26-30; and Alazraki et al., "Reliability of Radionuclide Angiography and Renography to Detect Varying Degrees of Impaired Renal Artery Flow". In: Bischof-Delaloye A, and Blaufox MD, eds., Radionuclides in Nephrology, Karger, New York (1987), pp. 82-86. It has been shown that the ratio of the slopes of the initial ascending portion of the renal time-activity curve is proportional to the relative renal blood flow. Ford et al., "The Radionuclide Renogram as a Predictor of Relative Renal Blood Flow", Radiology (1983) 149:819-821. These methods continue to prove clinically useful even though they face limitations such as dependence on the shape of injected activity, recirculation effects, and distribution of tracer to other compartments. Ash et al., "Quantitative Assessment of Blood Flow in Paediatric Recipients of Renal Transplants", J. Nucl. Med. (1988) 29:791-792.

More recently, attempts have been made to improve the methods described above by deconvolving the input-output time activity curves recorded by dynamic scintigraphy and thereby reduce dependence on empirical approximations. Nimmon et al., "Practical Application of Deconvolution Techniques to Dynamic Studies", In: Medical Radionuclide Imaging. Vienna:IAEA 1981; pp. 367-380; and Russell, "Estimation of Glomerular Filtration Rate Using $^{99m}$Tc DTPA and the Gamma Camera", Eur. J. Nucl. Med. (1987) 12:548-552.

Several attempts have been made to determine flow directly from measured time activity curves without involving deconvolution procedures. Quantitative measurements of renal blood flow obtained by combining scintigraphy and ultrasound have been reported. Lear et al., "Quantitative Measurement of Renal Perfusion Following Transplant Surgery", J. Nucl. Med. (1988) 29:1656-1661. Real time ultrasound was used to determine the volume of the femoral artery from which the activity in a region of interest was measured. Thus, the activity of the tracer per unit volume of arterial blood, $C_a(t)$, was used as the input function and $A_k$ was the measured activity over the kidney. T was set to 5 sec. The equation utilized was $$F = A_k(T) / \int_0^T C_a(t) \cdot dt \quad \text{(A)}$$

an approximation to the convolution integral $$A(t) = \int_0^t h(t - t') \cdot B(t') \cdot dt'. \quad (B)$$

Equation A represents a modification of the formulation proposed to describe the uptake of a tracer in an organ from measurements of the arterial and venous concentrations (input B(t) and output A(t)). Meier and Zierler, "On the Theory of Indicator Dilution Method for Measurement of Blood Flow and Volume", J. App. Physiol. (1954) 6:731-744.

Since such measurements are available only with invasive techniques it has been proposed that the output function, i.e. the concentration of tracer in the venous efflux could be set to zero during the very early interval of tracer uptake. Mullani and Gould, "First-pass Measurements of Regional Blood Flow with External Detectors", J. Nucl. Med. (1983) 24:577-581. This assumption leads to equation A. Comparing equation A with equation B, $h(t-t')$ must be set to constant=F. In other words, tracer particles accumulate at a constant rate which implies that, under physiological conditions, tracer particles must remain within the region or organ supplied by the input. This holds true only when microspheres are used.

It has been reported that the kidney time activity curves have the same shape as the integrated arterial time activity curves. Peters et al., "Noninvasive Measurement of Renal Blood Flow (RBF) with DTPA", J. Nucl. Med. (1987) 28, #4(suppl):646. Even though under these circumstances the measured organ activity is proportional to blood flow, F, and the integral of the arterial concentration over time, it is questionable if equation A, even when integrated over the first time points, is appropriate for estimating blood flow to the organ. This is because mean transit time for most vascular beds, including the kidney are such that clinically useful tracers such as DTPA and hippuran, which are not administered as microspheres, leave the organ quickly.

Although several methods exist for performing deconvolution numerically, the methods are plagued by instabilities in the presence of noise. Szabo et al., "Effects of Statistical Noise and Digital Filtering on the Parameters Calculated From the Impulse Response Function", Eur. J. Nucl. Med. (1987) 13:148-154.

SUMMARY OF THE INVENTION

The present invention introduces a noninvasive method of determining function of a target organ of a subject using a pre-calibrated detector/measuring system or an imaging system (hereinafter measuring system). The method contains the steps of (1) introducing into the subject's circulatory system a bolus of indicator (tracer or contrast media, hereinafter tracer) capable of being monitored by the measuring system; (2) obtaining with the precalibrated measuring system at least one data set or image of the time activity response of the system/organ (hereinafter organ) expressed as A(t); (3) concurrently with step 2 above, obtain a data set or image of the time activity response of the heart or great vessels (hereinafter heart) expressed as B(t); (4) measuring the absolute amount, concentration, activity, or density (hereinafter amount) of the indicator in a known volume of a blood/plasma sample (hereinafter blood) or samples withdrawn from the subject at a known time (t) or times ($t_n$) which measurement(s) are used to normalize or convert the time activity response data recorded from the heart or great vessels (step 3 above) and be expressed as B(t) [input function] and (5) deconvolving A(t) and B(t) by the equation $$A(r,t) = \int_0^t h(r,t - t') \cdot B(t') \cdot dt',$$

deriving h(t), the linear response function (LRF) by deconvolution. Although other methods may be suitable, the preferred method of deconvolution is the deconvolution by orthogonal polynominals (DOP) method as described below. The present invention can also be used to determine blood flow rate and organ clearance.

This invention also teaches collecting a set of up to 60-120 images of both A(t) and B(t), said set of images depicting the time course of the passage of the tracer through the organ. After extraction of the LRFs, novel images can be synthesized showing time course of the passage of the indicator through the organ as if there is no recirculation of the tracer. This set of images, synthesized from the original set of images, is stored on disc, retrieved, and processed for display as still photographs or in cine mode. The information in the synthesized set of images can be compressed into single functional images representing the peak, plateau, and/or first moment (mean transit time) of the LRF or any and all of the presently undefined parameters of the LRF. The functional images derived from the LRF reveal both anatomic and physiologic characteristics of the organ.

BRIEF DESCRIPTION OF THE DRAWINGS

FIG. 8 depicts gamma camera scintigrams of a patient's thyroid.

FIG. 11 depicts images of the LRF function of the thyroid.

DETAILED DESCRIPTION OF THE INVENTION

Introduction

Figure 1:
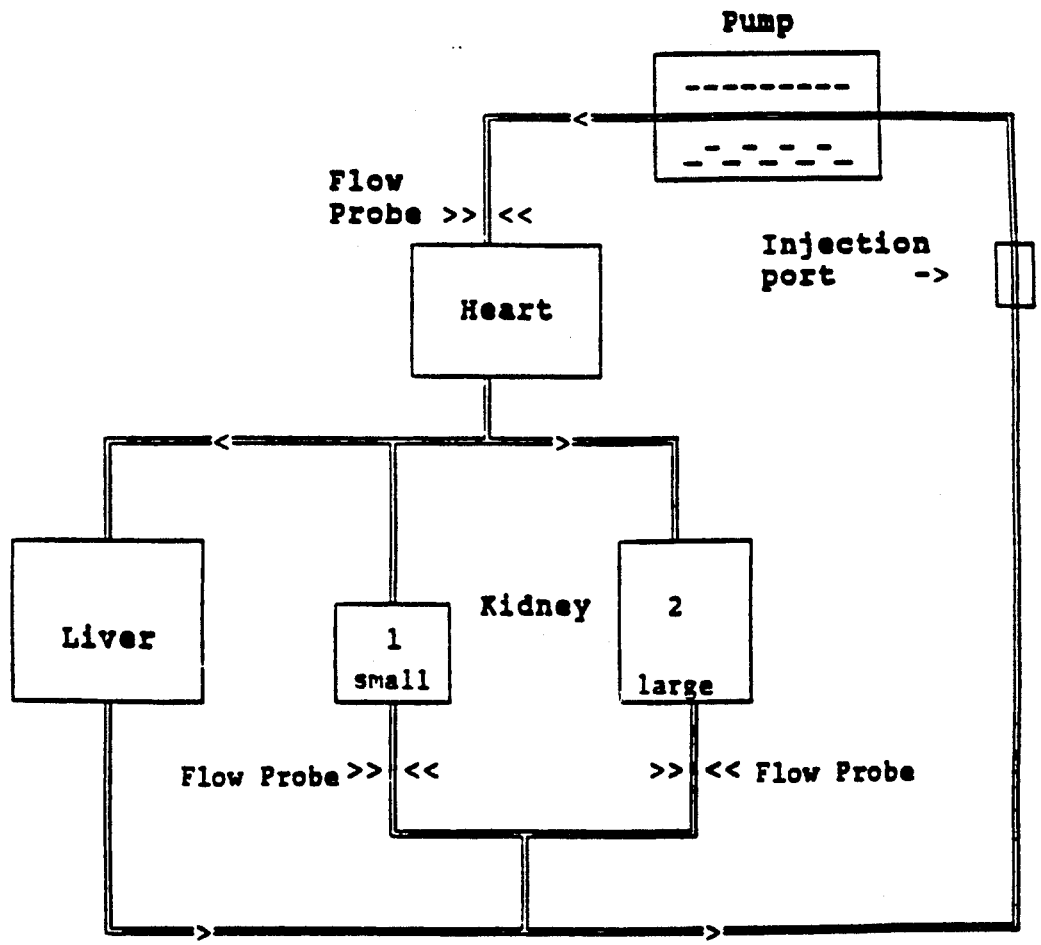
FIG. 1 illustrates the design of the phantom circulatory device which was used to validate the LRF peak method.

It has now been found that the application of the deconvolution method to medical imaging of animals including man is greatly enhanced by pre-calibration of the measuring system and that, surprisingly, information regarding organ function such as blood flow rate and organ clearance rate can now be empirically determined. The approach described in the present invention for obtaining absolute organ function characteristics from tracer time activity data depends on at least five key ingredients. These are: (1) data acquisition; (2) calibration of the detecting measuring systems to convert organ counts/sec to mCi/organ; (3) deconvolution to obtain the LRF in units of flow, ml/sec; (4) interpretation of the phases of the LRF; and (5) functional imaging.

1. Data Acquisition

A tracer is injected into the circulatory system of a subject, and the simultaneous and subsequent tracer time activity data from both the heart or great vessels (input function) and from the target organ (output function) are acquired by a precalibrated detecting system and stored for further manipulations.

Suitable tracers include but are not limited to all diffusible and nondiffusible tracers suitable for medical imaging. Tracers can be radioactively labeled for instance by gamma-emitting and positron emitting substances. In the case of magnetic resonance imaging, a contrast agent may not be necessary however, paramagnetic substances such as gadolinium may be used. In the case of digital subtraction radiography a number of non-radioactive iodine containing contrast media are available.

Tracers are either diffusible or non-diffusible. Non-diffusible tracers are those which are confined to the blood vessels and pass directly through the organ. Diffusible tracers can either passively diffuse across blood vessels but are not taken up by the cells or pass through the blood vessels and are taken up by the cells. If the diffusible tracer is not taken up by the cells it remains confined to the extracellular space.

Suitable systems include but are not limited to parts of the body irrespective of the organs such as the limbs. Suitable organs include but are not limited to kidneys, heart, liver, brain, bone, thyroid, pancreas, lungs, central nervous system, or parts thereof, by organ we mean the organ itself and any blood vessels attached thereto. Suitable measuring systems include but are not limited to scintillation detectors, gamma cameras, single photon emission tomography (SPECT), positron emission tomography (PET), nuclear magnetic resonance imaging (MRI) and digital subtraction radiography (DSR).

2. System Calibration

A linear measuring system is pre-calibrated by determining its ability to detect a known quantity of a tracer and dividing the value obtained by the known value to obtain the calibration factor. The calibration factor is then defined as the relationship between the measuring system's response and the known quantity, the "standard".

For example, to calibrate a scintillation probe or gamma camera, a model (phantom) organ is filled with a known quantity of tracer in absolute units (e.g. weight, weight/volume, mCi), and placed in a scattering medium such as lucite or water to simulate attenuation of a subject such as a human body at approximate organ depths. The tracer is then measured by the detector. The measured value is then divided by the known value to determine the "sensitivity" of the measuring system. The sensitivity is called $F_G$, which is the factor used to multiply all elements of the observed recorded time activity thereby converting the activity response (data set or image element) of the target organ to absolute units of quantity. The final result of multiplying $F_G$ by the observed recorded time activity response is known as A(t), the output function.

The calibration of the measuring system is only an approximation for any given patient when organ size and depths vary from that used to calibrate the measuring system. Methods have been developed for generating buildup factors to generate attenuation corrected images for use in absolute volume and activity measurements. See e.g. Siegel et al., "The Buildup Factor: Effect of Scatter on Absolute Volume Determination", J. Nucl. Med. (1985) 26:390–394.

For calibration of SPECT, PET, MRI, and DSR, a cylinder with known dimensions and volume sufficient to cover the expected field of view is filled with a known quantity of tracer. The measuring system is then used to measure the tracer. The three dimensional data acquired by these measuring systems are reconstructed to provide a map of calibration factors which may be spatially dependent or variant. These calibration factors, in accord with their localization within the defined space of the target organ space, are used to multiply all elements of the observed recorded time thereby converting it to activity response in a respective voxel of the target organ to absolute units of quantity A(t).

As an example, in the case where a large field gamma camera is used, it can be calibrated by means of acquisition of a static study of a phantom with known activity to give the calibration constant $F_G$ in (mCi.sec)/(counts.organ). $F_G$ is used to multiply the target organ's dynamic time activity data, usually recorded by the gamma camera as counts/sec, and thereby convert it to absolute activity (mCi/image element). These converted data are known as A(t), the output function.

To normalize and convert the observed dynamic time activity response recorded from the heart or great vessels, a factor, $F_W$, in (mCi.sec)/(ml counts) must be determined. To accomplish this, the absolute quantity of the tracer is determined for a known volume of a sample or samples of the subject's blood withdrawn at time (t) or times ($t_n$) after the injection of the tracer but during the time that the dynamic time activity response from the heart or great vessels is being acquired. It is preferred that the blood sample is taken at approximately t≧1 minute because at this time the tracer has reached equilibrium in the blood. The blood can be obtained from any site although it is preferably obtained from a vein such as the antecubital fossa. For a radioactive tracer, the radioactivity in blood sample(s) is then measured in a previously calibrated well-counter (liquid scintillation counter) and expressed as mCi/unit volume. Since the actual amount of tracer in the heart or great vessels is directly determined by the measuring system, the factor, $F_W$, in (mCi·sec)/(ml·counts) relating the observed recorded activity from the heart or great vessels at time (t) or times ($t_n$) to the actual absolute quantity of tracer present in each unit volume of the subject's blood is easily determined. This factor, $F_W$, is used to multiply, and thereby convert the observed recorded dynamic time activity from the heart or great vessels into units of absolute quantity of indicator/ml of blood. These converted data are known as B(t), the input curve.

3. Deconvolution Technique

Introduction

The stimulus-response of an organ, denoted as G(r,t), where r represents the location r in the organ, and t the time after injection, completely describes the kinetics of the tracer used to identify specific characteristics of that organ. G(r,t) can be obtained by measuring simultaneously the activity in the blood, B(t), and the activity in the target organ, A(r,t). The general equation to describe the tracer transport from the blood to the organ is given by $$A(r,t) = \int_0^t G(r,t,t') \cdot B(t') \cdot dt' \quad (C)$$

G(r,t,t') is called Green's function and varies with the location r in the organ and the time t. If the anatomical and physiological properties of the organ do not change during the interval in which it is being observed and data are being acquired, the system is assumed to be stationary and linear. Thus, in the special case where the system is in a steady state, G(r,t,t') reduces to a single dependence on t−t' which results in $$A(r,t) = \int_0^t h(r,t,t') \cdot B(t') \cdot dt' \quad (B)$$

where h(r,t−t')=G(r,t,t'). A(r,t) therefore depends only on the difference t−t' instead of on both times t, t' explicitly. Inversion of equation B, to determine h(t), is commonly called deconvolution, and h(t) is the LRF.

Several methods of deconvolution are available. These include the divided Fourier method, the matrix method, and discrete deconvolution applied in large regions of interest. None of these methods have been applied to deconvolve pixel or voxel images. Although these methods would theoretically be acceptable they are unable to handle the degree of noise unavoidably present in medical imaging. The preferred method of deconvolution is by the use of the DOP method. It has now been shown that the DOP method is the only known method capable of application to series of images and image elements. The DOP method works well in the presence of noise, reliably and reproducably performing deconvolution.

3.1 DOP

It is assumed that A, B and $h_L$ in equation (1)

$$A(x,y,t) = \int_0^t h_L(x,y,t - t') \cdot B(t') \cdot dt' \quad (1)$$

are differentiable functions over the time period of the study T, with the exception that $h_L$ has a delta function partition which reflects the activity within the blood volume external to the boundaries of the target organ but included within an imaged pixel x,y. Note that the notation x,y is equivalent to the notation r in equation B and is a synonym for describing spatial orientation of data measured by different measuring systems such as but not limited to a region of interest, pixel and voxel. Thus, the LRF in equation (1) is given by:

$$h_L(x,y,t) = h(x,y,t) + c(x,y) \cdot \delta(t) \quad (2)$$

where h is the "true" organ linear response function, c is the activity within the blood pool of the tissue being imaged, i.e. the amount of activity not included in the target organ, and δ is the Dirac delta function. Stritzke et al., "Funktionsszintigraphie: Eine einheitliche Methode zur Quantifizierung von Stoffwechsel und Funktion in Organen", Nucl. Med. (1985) 24:211-221. The Dirac delta function in equation (2) represents a singularity, meaning that the linear response function reaches an infinitely high function value at time zero. Standard deconvolution methods including the DOP method cannot handle such singularities explicitly. Therefore, it is necessary to develop a form of equation (1) which can be deconvolved without the negative effects associated with this singularity. One way to accomplish this is to introduce the accumulative residence time distribution function $H_L$, which is defined as:

$$H_L(x,y,t) = \int_0^t h_L(x,y,t') \cdot dt' \quad (3)$$

Bassingthwaighte, "Circulatory Transport and the Convolution Integral", Mayo Clin. Proc.(1967) 42:137-154. Substituting equation (2) into equation (3), one obtains:

$$H_L(x,y,t) = c(x,y) + \int_0^t h_L(x,y,t') \cdot dt' \quad (4)$$

where it is observed that the delta function δ has been removed by integration. Then the integral of the activity I is defined as:

$$I(x,y,t) = \int_0^t A(x,y,t') \cdot dt'. \quad (5)$$

Using equation (1) and equation (3), equation (5) can be rewritten as:

$$I(x,y,t) = \int_0^t h_L(x,y,t - t') \cdot B(t') \cdot dt'. \quad (6)$$

In the following, the word image is used as an equivalent to spatial information obtained by any measuring system. The DOP method, like any deconvolution analysis method, requires discrete notation and interpolation to uniform temporal intervals. In other words, a series of scintigraphic images must be obtained concurrently with sampling of at least one blood sample. The data need to be acquired at constant time intervals. If, however, data are not obtained at uniform time intervals, interpolation of data has to be employed. The same process can be applied to the results obtained from the blood samples.

Hereafter, the symbol (o) indicates that the time sampling is not necessarily uniform. The dynamic study may consist of N images. For a given set of time points $0 \leq t_1{}^o \leq t_2{}^o \ldots \leq t_{p-1}{}^o \leq t_p{}^o \ldots \leq t_N{}^o = T$, the sampling of the scintigraphic images is defined as:

$$S^o(x,y,t_p{}^o) = \sum_{p-1}^{p} A(x,y,t') \cdot \Delta t', \text{ for } 1 \leq p \leq N \quad (7)$$

where A is the activity in terms of counts per unit time in pixel x,y as determined by the gamma camera at time $t_p{}^o$ post-injection. Any number of blood samples $B^o$ can be taken at times $t_i{}^o$ over the time period T of the study, but more than one sample is preferred to provide a more accurate result. The units of the samples $B^o$ are in activity per unit time measured in a well-counter.

With discrete sampling, equation (6) giving the integral of the activity can be written as:

$$I^o(x,y,t_n{}^o) = \sum_{m=1}^{n} S^o(x,y,t_m{}^o) \cdot \Delta t \quad (8)$$

where $S^o$ is the pixel count in the scintigram as defined in equation (7). The expansion of $I^o$ and $B^o$ using orthogonal polynomials which is used to deconvolve equation (6) requires equal time sampling. If necessary, linear interpolation is used to convert $I^o$ and $B^o$ to I and B sampled over U time points $t_n$ defined as $$t_n = (n-1) \cdot \Delta t, \, n = 1, 2, \ldots, U \quad (9)$$

with $\Delta t = T/(U-1)$ and $U \cdot \Delta t \leq T$. The linear interpolation of the sampled integral images $I^o$ into the uniformly time sampled integral images I can be conducted in the following way. First, a set of interpolation coefficients are calculated for each time point $t_n$ with $t_1 \leq t_2 \ldots \leq t_n \leq T$:

$$\alpha_n = (t_n{}^o - t_n) \cdot D_n{}^o \quad (10)$$
$$\beta_n = 1 + t_n \cdot D_n{}^o - t_n{}^o \cdot D_n{}^o$$
where:

$$D_n{}^o = \frac{1}{t_{n+1}{}^o - t_n{}^o}, \text{ for } t_n{}^o \leq t_n \leq t_{n+1}{}^o. \quad (11)$$

This is performed in the host computer. Then, the interpolation of the integral images is performed in the array processor as $$I(x,y,t_n) = \alpha_n \cdot I^o(x,y,t_{n+1}{}^o) + \beta_n \cdot I^o(x,y,t_n{}^o). \quad (12)$$

Using linear interpolation or cubic spline interpolation according to Spaeth, "Spline-DOP methoden zur Konstruktion Glatter Kurven und Flaechen (1928) R. Oldenburg Verlag Muenchen, Wien; and Press et al., "Numerical Recipes, The Art of Scientific Computing" (1986) Cambridge University Press, Cambridge, New York for the input function $B^o$, and replacing the integral with its approximation by a Riemann sum, equation (6) can be written as:

$$I(x,y,t_i) = \sum_{m=1}^{i} H_L(x,y,t_i - t_m) \cdot B(t_m) \cdot \Delta t. \quad (13)$$

Equation (13) is the final stochastic description of the tracer behavior in an organ and is independent of specific compartmental models. It is temporally deconvoluted to yield the integral of the response function $H_L$. Given $H_L$, h is derived by numerical differentiation.

A functional analytical solution of the convolution type integral equation can be obtained. With the assumption of square integrability of the functions $H_L$, B and I in the time interval $0 \leq t \leq T$ during the investigation, equation (13) can be written in Dirac notation (see below):

$$|I> = |B|H_L>. \quad (14)$$

The desired function $|H_L>$ is connected to the known (measured) function $|I>$ by the operator $|B|$. The method of inversion of equation (14) (deconvolution) which is used herein requires the introduction of a set of orthonormal polynomials $p_k(t)$, e.g. Legendre Polynomials as described in Arfken, "Mathematical Methods for Physicists" (1968) Academic Press, New York and London, calculated from their recurrence relation (Rodrigues' formula):

$$(k+1) \cdot p_{k+1} + k \cdot p_{k-1} = (2 \cdot k + 1) \cdot t \cdot p_k, \, |t| \leq 1 \quad (15a)$$

The $p_k(t)$ are normalized by setting $p_k(1) = 1$. For example, the first five functions can be written:

$$\begin{aligned} p_0(t) &= 1 \\ p_1(t) &= t \\ p_2(t) &= (3 \cdot t^2 - 1)/2 \\ p_3(t) &= (5 \cdot t^3 - 3 \cdot t)/2 \\ p_4(t) &= (35 \cdot t^4 - 30 \cdot t^2 + 3)/8 \\ p_5(t) &= (63 \cdot t^5 - 70 \cdot t^3 + 15 \cdot t))/8. \end{aligned} \quad (15b)$$

The $p_k(t)$ are orthogonal in the interval $1 \leq t \leq 1$ with the orthogonality-completeness relation $<p_m|p_n> = \delta_{mn} \cdot 2/(2n+1)$, where $\delta_{mn}$ is called the Kronecker delta and is defined by $\delta_{mn} = 0$ for $n \neq m$, $\delta_{mn} = 1$ for $n = m$. The polynomials $|p_k>$ are combined with B to produce the adjoint operator $|B|^+$ according to equation (43), below.

$$|b_k> = |B|^+ p_k>, \, k = 0, 1, 2, \ldots Z. \quad (16a)$$

In approximating the integral in equation (16) by a Riemann sum, $|b^k>$ can be written $$b_k(t_n) = \sum_{m=1}^{U-n} B(t_m) \cdot p_k(t_m + t_n) \cdot \Delta t \quad (16b)$$

where $n = 1, 2, \ldots, U$ corresponds to the time points $t_n$ (the time points including t are transformed into the interval $[-1,1]$) of the interpolated scintigraphic study). The $|b_k>$ are linearly independent but not necessarily orthogonal. From a set of linearly independent functions such as $|b_k>$ an orthonormal set of function $|c_m>$ over $[-1,1]$ can be constructed by simple linear combination of the $|b_k>$, such that $<c_i|c_j> = \delta_{ij}$, $i,j = 0, 1, 2, \ldots, Z$. In order to calculate the coefficients of the new linear combination $|c_k>$, the classical Gram-Schmidt method described in (Zurmuh, "Praktische Mathematik fur Ingenieure und Physiker" (1965)

Springer, Berlin, New York; and Delves and Mohamed, "Computational Methods for Integral Equations" (1985) Cambridge University Press, Cambridge, London, New York was modified by starting with the following set of equations:

$$|c_1\rangle = |b_1\rangle \quad (17a)$$
$$|c_2\rangle = a_{21} \cdot |c_1\rangle + |b_2\rangle \quad (17b)$$
$$|c_3\rangle = a_{31} \cdot |c_1\rangle + a_{32} \cdot |c_2\rangle + |b_3\rangle \quad (17c)$$
$$|c_4\rangle = a_{31} \cdot |c_1\rangle + a_{42} \cdot |c_2\rangle + a_{43} \cdot |c_3\rangle + |b_4\rangle \quad (17d)$$

The coefficients $a_{mi}$, $m=2\ldots Z$, $i=1\ldots m-1$, can be calculated by forming suitable scalar products $\langle c_i | c_j \rangle$ from each line in equation (17). Forming the scalar product $\langle b_1 | c_2 \rangle$ in equation (17b) yields $$\langle b_1 c_2 \rangle = 0 = a_{21} \cdot \langle b_1 | c_1 \rangle + \langle b_1 | b_2 \rangle \quad (18b)$$
$$a_{21} = -\langle b_1 | b_2 \rangle,$$

and forming the scalar products $\langle c_1 | c_3 \rangle$ and $\langle c_2 | c_3 \rangle$ in equation (17c) yields $$\langle c_1 | c_3 \rangle = 0 = a_{31} \cdot \langle c_1 | c_1 \rangle + a_{32} \cdot \langle b_1 | c_2 \rangle + \langle c_1 | b_3 \rangle \quad (18c)$$
$$\langle c_2 | c_3 \rangle = 0 = a_{31} \cdot \langle c_2 | c_1 \rangle + a_{32} \cdot \langle b_2 | c_2 \rangle + \langle c_2 | b_3 \rangle$$
$$a_{31} = -\langle b_1 | b_3 \rangle$$
$$a_{32} = -\langle b_2 | b_3 \rangle$$

For equation (17d) one obtains $$\langle c_1 | c_4 \rangle = 0 = a_{41} \cdot \langle c_1 | c_1 \rangle + a_{42} \cdot \langle c_1 | c_2 \rangle + a_{43} \cdot \langle c_1 | c_3 \rangle + \langle c_1 | b_4 \rangle \quad (18d)$$
$$\langle c_2 | c_4 \rangle = 0 = a_{41} \cdot \langle c_2 | c_1 \rangle + a_{42} \cdot \langle c_2 | c_2 \rangle + a_{43} \cdot \langle c_2 | c_3 \rangle + \langle c_2 | b_4 \rangle$$
$$\langle c_3 | c_4 \rangle = 0 = a_{41} \cdot \langle c_3 | c_1 \rangle + a_{42} \cdot \langle c_3 | c_2 \rangle + a_{43} \cdot \langle c_3 | c_3 \rangle + \langle c_3 | b_4 \rangle$$
$$a_{41} = -\langle c_1 | b_4 \rangle$$
$$a_{42} = -\langle c_2 | b_4 \rangle$$
$$a_{43} = -\langle c_3 | b_4 \rangle$$

and generally:

$$a(m,j) = -\langle c_j | b_m \rangle, \quad m=1\ldots Z, \quad j=1\ldots m-1 \quad (18e)$$

In order to form an orthonormal set of functions $|c_m\rangle$, the $a_{mi}$ equation (18e) must be divided by their norm factors. With these factors a new set of coefficients is calculated by $$a_{1,1} = \langle b_1 | b_2 \rangle^{-\frac{1}{2}} = \left( \int_{-1}^{1} b_1(t') \cdot b_1(t') \cdot dt' \right)^{\frac{1}{2}} \quad (19a)$$

where $\|b_1\| = \langle b_1 | b_1 \rangle$ denotes the norm.

$$a_{m,j} = \frac{a_{mj}}{\left( \langle b_m | b_m \rangle - \sum_{i=1}^{j} a_{mi}^2 \right)^{\frac{1}{2}}}, \quad (19b)$$

$$j = 1, 2, \ldots, m-1 \quad m = 2, 2, \ldots, z$$

$$a_{m,m} = \frac{1}{\left( \langle b_m | b_m \rangle - \sum_{i=1}^{m-1} a_{mi}^2 \right)^{\frac{1}{2}}}, \quad (19c)$$

$$m = 2, 2, \ldots, z$$

Hence, the set of equ.17 can now be rewritten:

$$|c_1\rangle = a_{11} \cdot |b_1\rangle \quad (20a)$$
$$|c_2\rangle = a_{21} \cdot |c_1\rangle + a_{22} \cdot |b_2\rangle \quad (20b)$$
$$|c_3\rangle = a_{31} \cdot |c_1\rangle + a_{32} \cdot |c_2\rangle + a_{33} \cdot |b_3\rangle \quad (20c)$$
$$|c_4\rangle = a_{41} \cdot |c_1\rangle + a_{42} \cdot |c_2\rangle + a_{43} \cdot |c_3\rangle + a_{44} \cdot |b_4\rangle \quad (20d)$$

This function set can easily be rearranged to $$|c_1\rangle = \tau_{11} \cdot |b_1\rangle \quad (21a)$$
$$|c_2\rangle = \tau_{21} \cdot |b_1\rangle + \tau_{22} \cdot |b_2\rangle \quad (21b)$$
$$|c_3\rangle = \tau_{31} \cdot |b_1\rangle + \tau_{32} \cdot |b_2\rangle + \tau_{33} \cdot |b_3\rangle \quad (21c)$$
$$|c_4\rangle = \tau_{41} \cdot |b_1\rangle + \tau_{42} \cdot |b_2\rangle + \tau_{43} \cdot |b_3\rangle + \tau_{44} \cdot 0 |b_4\rangle \quad (21d)$$

or $$|c_m\rangle = \sum_{i=1}^{m} \tau_{mi} \cdot |b_i\rangle, \quad m = 1, 2, \ldots, z \quad (22)$$

where the $\tau_{mi}$ are given by:

$$\tau_{11} = a_{11} \quad (23)$$
$$\tau_{21} = a_{21} \cdot a_{11}$$
$$\tau_{22} = a_{22}$$
$$\tau_{31} = a_{31} \cdot a_{11} + a_{32} \cdot a_{21} \cdot a_{11}$$
$$\tau_{32} = a_{32} \cdot a_{21}$$
$$\tau_{33} = a_{33}$$
$$\tau_{41} = a_{41} \cdot a_{11} + a_{42} \cdot a_{21} \cdot a_{11} + a_{43} \cdot a_{31} \cdot a_{11} + a_{43} \cdot a_{32} \cdot a_{21} \cdot a_{11}$$
$$\tau_{42} = a_{42} \cdot a_{22} + a_{43} \cdot a_{32} \cdot a_{22}$$
$$\tau_{43} = a_{43} \cdot a_{33}$$
$$\tau_{44} = a_{44}$$

It should be noted that an orthogonal function system, if multiplied by an arbitrary constant $k \neq 0$, remains an orthogonal function system. Thus, the coefficients $\tau_{mi}$ calculated from equation (23) can be used to construct a second set of functions using the Legendre polynomials calculated in equation (15)

$$|d_m\rangle = \sum_{i=1}^{m} \tau_{mi} \cdot |p_i\rangle \quad (24a)$$

or equivalently $$d_m(t) = \sum_{i=1}^{m} \tau_{mi} \cdot p_i(t) \quad (24b)$$

which is also an orthogonal function system. The $|c_m\rangle$ and $|d_m\rangle$ are now being used to invert the integral equation (14). For this purpose start with the completeness or closure condition. In: Liboff "Introductor Quantum Mechanics", Holden-Day, California, 1980.

$$\sum_{m=1}^{z} |c_m\rangle\langle c_m| = 1 \quad (25)$$

(note that $|c_m\rangle\langle c_m|$ is an operator). Now it can be writen $|H_L\rangle$ as the identity $$|H_L\rangle = \sum_{m=1}^{z} |c_m\rangle\langle c_m|H_L\rangle. \quad (26)$$

With insertion of equation (22) into equation (26), we find $$|H_L\rangle = \sum_{m=1}^{z} |c_m\rangle \cdot \sum_{n=1}^{m} \tau_{mn}\langle b_n|B|H_L\rangle. \quad (27)$$

With equation (16) follows $$|H_L\rangle = \sum_{m=1}^{z} |c_m\rangle \cdot \sum_{n=1}^{m} \tau_{mn}\langle p_n|B|H_L\rangle \quad (28)$$

and using equation (24) and equation (14) the final result is $$|H_L\rangle = \sum_{m=1}^{z} |c_m\rangle\langle d_m|I\rangle. \quad (29)$$

The expression for accumulative residence time distribution function $|H_L\rangle$ can be written for computer implementation in the final form $$H_L(x,y,t_n) = \sum_{m=1}^{z} c_m(t_n) \cdot \left( \sum_{n=1}^{U} d_m(t_n) \cdot I(x,y,t_n) \cdot \Delta t \right). \quad (30)$$

The LRF can be calculated by numerical differentiation of equation (24)

$$h(x,y,t) = \frac{\partial H_L(x,y,t)}{\partial t}$$

and using following five point formula Hildebrand, "Introduction to Numerical Analysis, 2nd ed. New York: McGraw Hill, 1974 p. 111.

$$H_0' = \frac{1}{10 \cdot \Delta t} (-2 \cdot H_{-2} - H_{-1} + H_1 + 2 \cdot H_2) \quad (31)$$

According to the definitions given in equation (3) and equation (4) the partition blood volume can be determined by $$c(x,y,)=H(x,y,t=0). \quad (32)$$

Computer implementation of the DOP method is carried out by the following step-by-step procedure:

1. Calculate the functions $|c_m\rangle$ according to equations (15)–(23) where the $|c_m\rangle$ represent a Z·U matrix, Z denotes the number of polynominals, and U the number of images:

$$\begin{matrix} c_1(t_1) \; c_1(t_2) \; c_1(t_3) \; \ldots \; c_1(t_U) \\ c_2(t_1) \; c_2(t_2) \; c_2(t_3) \; \ldots \; c_2(t_U) \\ c_3(t_1) \; c_3(t_3) \; \ldots \\ \vdots \end{matrix} \quad (33)$$

$$c_Z(t_1) \; c_Z(t_2) \; c_Z(t_3) \; \ldots \; c_Z(t_U).$$

2. Calculate the orthogonal set of functions $|d_m\rangle$ according to equation (24) with $$\begin{matrix} d_1(t_1) \; d_1(t_2) \; d_1(t_3) \; \ldots \; d_1(t_U) \\ d_2(t_1) \; d_2(t_2) \; d_2(t_3) \; \ldots \; d_2(t_U) \\ d_3(t_1) \; d_3(t_3) \; \ldots \\ \vdots \\ d_Z(t_1) \; d_Z(t_2) \; d_Z(t_3) \; \ldots \; d_Z(t_U). \end{matrix} \quad (34)$$

3. If the scintigraphic images are not recorded at uniform time intervals, integrate and interpolate the scintigrams according to equations (8)–(12).

4. Calculate a new set of values $|f_m\rangle$ representing the second sum term in equation (29):

$$f_1(x,y) = \sum_{i=1}^{U} d_1(t_i) \cdot I(x,y) \quad (35)$$

$$f_2(x,y) = \sum_{i=1}^{U} d_2(t_i) \cdot I(x,y)$$

$$\vdots$$

$$f_z(x,y) = \sum_{i=1}^{U} d_z(t_i) \cdot I(x,y).$$

5. Calculate equation (29) in the form:

$$H(x,y,t_i) = \sum_{m=1}^{z} c_m(t_i) \cdot f_m(x,y). \quad (36)$$

6. Finally calculate the linear response function h by numerical differentiation according to equation (31).

In steps 1 and 2, no image data is required. The elements of $|c_m\rangle$ and $|d_m\rangle$ is only dependent on the input function and the type of polynomials. The computation can be performed in the host computer within a few seconds. Use of an array processor can speed this phase of the implementation, but this is not the major computational load of the DOP method. Steps 3, 4 and 5 require access to the entire image set of 60–120 images. In the mini-computers typically used in nuclear medicine, it is usually not possible to have all of these images simultaneously resident in memory. To avoid multiple disk transfers of the data set, it has been suggested to depict a subset of the image data (e.g. 1/16 of each image) for complete data processing through steps 3–6 which are the number "crunching" intensive portion of the DOP method. To test the concept of the invention, these have been implemented on an array processor (Analogic, AP 400).

For yet another way to illustrate the DOP method, the Dirac notation, proven to be a powerful tool in solving our inverse problem, is described below. Given two functions k and g continuously dependent on a set of variables $k=k(t)$ and $g=g(t)$, and defined in the interval $a \leq t \leq b$, the scalar or inner product will then be given by $$<k/g> = \int_a^b k(t') \cdot g(t') \cdot dt'. \quad (37)$$

The $|g>$ (or ket) can then be interpreted as a column matrix with the components $g_i$ and $>k|$ (or bra) as a row matrix with the components $k_i$. Assuming the functions $<k|$ and $|g>$ to be elements of the Hilbert space [linearity, existence of scalar product equation (37), existence of a length (norm), and completeness], the functions $<k|$ and $|g>$ can be called vectors. This is due to the similarity of this concept to the definition of two finite-dimensional vectors. Let h be a linear operator acting on $|g>$. This may be written in either of two equivalent ways $|h|g>$ or $|hg>$. The operator $|h|$ can be quite general, and this operation is given as $$|h|g> = \int_0^t h(t - t') \cdot g(t') \cdot dt'. \quad (38)$$

The relation $$<h|g> = <g|h|+ \quad (39)$$

is often called the "turn over rule", where $|h|+$ is called the adjoint operator to $|h|$. In the following it will be shown how to derive the adjoint operator from equation (37) and equation (38). With these equations it follows that $$<k|h|g> = \int_0^T k(t) \cdot \int_0^t h(t - t') \cdot g(t') \cdot dt \cdot 'dt. \quad (40)$$

By exchanging the order of integration as described by the Fubinis theorem, Liboff, "Introductory Quantum Mechanics", the Holden-Day, Calif., 1980 equation (40) can be written as $$<k|h|g> = \int_0^T g(t') \cdot dt' \cdot \int_{t'}^T h(t - t') \cdot k(t) \cdot dt \quad (41)$$

and by exchanging the variables t'·dt' with t·dt it follows $$<k|h|g> = \int_0^T g(t) \cdot dt \cdot \int_t^T h(t' - t) \cdot k(t') \cdot dt'. \quad (42)$$

Writing equation (42) in Dirac notation we find $$<k|h|g> = <g|h|+k>. \quad (43)$$

The comparison of equation (43) with equation (38) delivers the final formulation for the adjoint operator $|h|+$:

$$|h|+g> = \quad (44)$$

$$\int_0^{T-t} h(t' - t) \cdot g(t') \cdot dt = \int_0^T h(t') \cdot g(t' + t) \cdot dt'.$$

Equation (44) was used to calculate a function system $b_k = |B|+p_k>$ equation (16), where B is the blood input function and $p_k$ is a set of Legendre polynomials.

3.2 Computational Processing of the Deconvolution

It has now been shown that the method based on DOP leads to an estimation of the linear response function of a single pixel, voxel, or any defined region in space. The DOP method described has been developed for use with an array processor. It has been divided into a preprocess step and the actual time consuming estimation of the LRF in each pixel. The preprocess step can be performed in the host computer and needs numerical values of a well defined input function. It then performs the computation of orthogonal functions of the degree Z, the estimation of an adjoint operator, and an orthonormalization process. This preprocess results in two Z·U matrices, where U is the number of the images and Z the degree or number of the polynomials used. The matrix values do not depend on any measurements of the organ data. Although the rest of the process needs only the operations of multiplication and summation of the image data with the matrices determined from the preprocess, it is time consuming and therefore ideally suited for use with the array processor.

For the computers usually available in nuclear medicine, the DOP method can be performed in blocks of values. This is usually the preferred method because of limitations of the host's and array processor's memory. This causes some inefficiencies in terms of full computation speed of the array processor, but avoids multiple disk to memory transfers of the scintigraphic data. The computation is straightforward and does not need any a priori information in terms of shape and periodicity of the scintigraphic data. The LRF images are calculated using 15 Legendre polynomials and the scintigraphic images interpolated into 60 to 120 images. The computation time on a PDP-11/23 without hardware floating point arithmetic is about 3 hours. This time is decreased to 45 minutes using a PDP-11/34 with floating point arithmetic and cache memory, and is further dramatically decreased by the implementation of the DOP method on a PDP-11/34 with floating point arithmetic, cache memory, and array processor. With the latter configuration, the computation intensive part of the DOP method is reduced to 3 minutes for the full computation of the LRF in floating point format. The time to compute a LRF in 120 images (64×64 matrix size) on a VAX-11/750 with hardware floating point and 8MB of memory is 10–20 minutes depending on the clinical load on the computer. As computer speed and abilities increase the calculations involved can be done more rapidly.

4. Linear Response Function and its Physiological Significance

Figure 3:
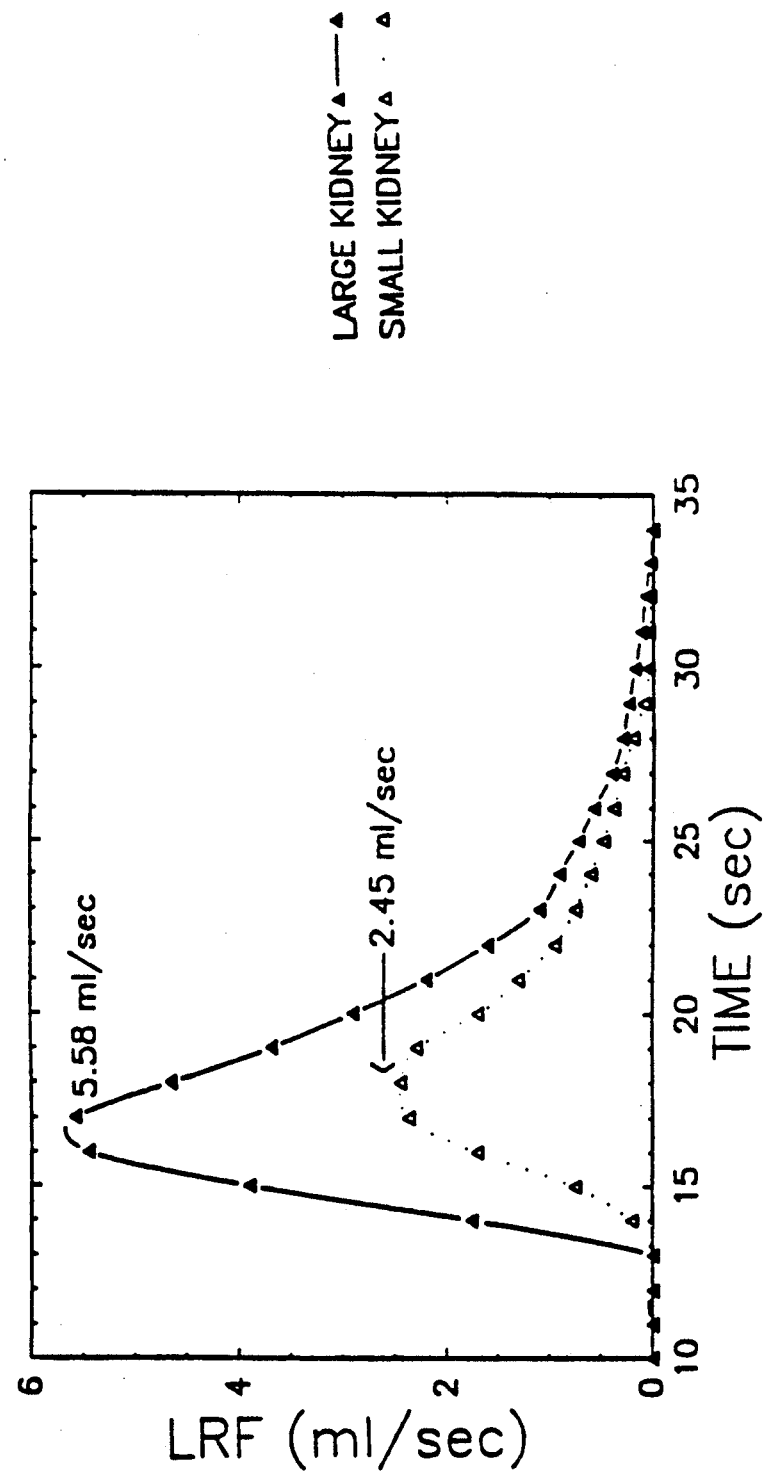
FIG. 3 depicts LRF curves obtained by deconvolution of the data shown in FIG. 2. Symbols used are the same as those in FIG. 2.
Figure 12:
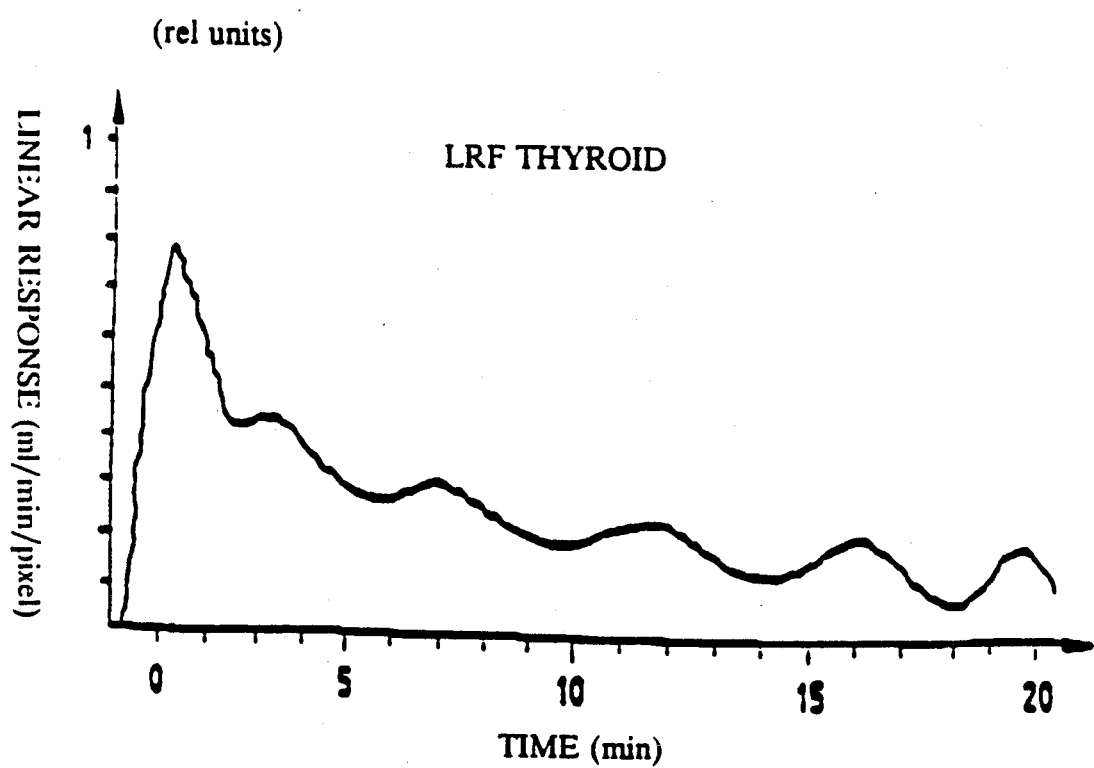
FIG. 12 illustrates a time curve of the LRF in an image element of the thyroid showing $^{123}$Iodine clearance rate from 5 to 20 minutes after the injection.

Surprisingly, there are several distinct components of the LRF curve which have now been found to reveal information about organ function heretofore unavailable by noninvasive techniques. The peak of the LRF curve represents the blood flow to the organ as shown in FIG. 3. The organ's clearance rate of a diffusible tracer can be measured directly from the value of the plateau of the LRF curve as shown in FIG. 12.

Two types of clearance information can now be calculated depending on the type of tracer used. In the case of a diffusible tracer which diffuses only into the extracellular but not the intracellular space, the blood flow rate to the organ and the organ's passive capacity to clear the traces from the blood can now be measured. In the case of tracers which are able to diffuse into the intracellular space, the LRF curve can provide a measure of the intrinsic functional capacity of the organ's cells to clear the tracer from the blood. The measurements utilizing tracers diffusible into the intracellular space are particularly useful in monitoring the pharmacological efficacy of therapeutic agents and in providing diagnoses and prognoses of organ function. For instance, a comparison of FIGS. 3 and 12 show the difference between an LRF curve obtained in a phantom machine utilizing the equivalent of a non-diffusible tracer (FIG. 3) and a diffusible intracellular tracer (FIG. 12) in a subject. Notice in FIG. 3 the descending portion of the LRF curve reaches zero after approximately thirty-five seconds whereas the descending portion of the LRF curve in FIG. 12 does not reach zero even after twenty minutes.

Additional information of physiologic significance may be obtained from data on the first moment or transit time of the LRF equation (E).

5. Functional Imaging

As described above, the LRF of an organ, as obtained by temporal deconvolution using the DOP method, is a set of images derived from originally acquired dynamic images as described in sections 1 and 2 above, describing the kinetics of an indicator in response to a very short stimulus such as a bolus injection of an tracer. After using calibration procedures as described above, the LRF represents the manner by which the organ characteristically handles the tracer in terms of a quantity of flow expressed in absolute units, volume per unit time. This quantity could be the blood flow to the organ, or the rate at which the tracer is cleared by the organ. These LRF images are stored on disk and have the same data format as the acquired original dynamic images. Heretofore functional images representing absolute blood flow rate and clearance rates which have physiological significance have not been available.

There are a number of ways to create functional images from the LRF. For instance standard image processing techniques as are available in all commercial imaging systems can be used. Standard image processing techniques comprise operations including but not limited to displaying up to 64 images and more on one screen, displaying images in cine mode, drawing region of interests (ROIs), generating time activity curves, adding images and multiplying images with a scalar. A functional image representing blood flow can be created by drawing a region of interest which includes the whole or any part or parts of the target organ, and generating the time course of the LRF values within this region. For example, the LRF can be determined from 120 LRF images consisting of 120 data points. The point in time at which the LRF value reaches a peak determines the image number from which blood flow rate can be derived. The image at which the curve reaches the peak can be marked and separately displayed on screen. Image processing techniques and statistical methods can be applied to determine the organ's contour, and the sum of all values within this contour which represent the total blood flow to the organ. The image can be labeled, photographed and stored on disk for archival purposes. Similar procedures are applicable to determine the plateau image of a LRF which represents the rate at which the organ clears the tracer from the blood. The functional images can be expressed in terms of absolute blood flow rate and clearance rate which signify the physiological status of the organ.

Another embodiment in the present invention is the derived quantity of transit time of the indicator through the organ. A transit time image can be composed by calculating the first moment from the time course of the LRF values in each image. For example, to calculate a transit time image from a LRF set of 120 images each consisting of 64×64 matix points, 4096 curves each consisting of 120 data points are necessary to be processed. Another means for creating functional images is to perform the described data processing procedures separately in a stand-alone computer with an associated menu. The result of this processing is one or more functional images which can be displayed as described above. These too can be stored on disk for archival purposes. These measurements would not otherwise be readily available except by exposing a subject to the medically unacceptable risks associated with the invasive methods currently available.

In summary functional images are the graphic illustration of the LRF at any point in time after the injection of the tracer. These functional images will reveal both anatomic and physiologic characteristics. For example, the distribution of the tracer will give shape and structure of the target organ. Choosing a particular phase of the LRF, such as its peak, plateau, or first moment will characterize absolute rates of blood flow, tracer clearance or transit time in each image element.

The following examples are meant to further illustrate but not limit the present invention.

EXAMPLE 1

Circulatory Phantom Model

To validate our method to determine perfusion rate using dynamic scintigraphy, we designed a circulatory phantom to produce known "organ functions" to be compared to the measured organ function. The phantom contains a pulsatile pump, "vascular" conduits, an injection port proximal to a "heart" or input chamber, target "organ" chambers, and electromagnetic flow meters (FIG. 1).

In FIG. 1, box 1 represents the small right "kidney" with a volume of 13 ml while box 2 represents the large left "kidney" with a volume of 26 ml. A calibrated electromagnetic flow probe measures the flow rate from each kidney. The "heart" chamber contains a volume of 132 ml. A calibrated electromagnetic flow probe measures the inflow rate to the "heart."

To perform the experiments utilizing the phantom, a pump (Sigma Motor, Middleport, N.Y.) fitted with latex rubber tubing (⅛ inch internal diameter) perfused the phantom organs with normal saline (0.8%) via "vascular" conduits consisting of tygon tubing which contained 180 ml of fluid between the "heart" and "renal artery" bifurcations and 25 ml in each "renal artery." The injection port allowed for rapid bolus injection of $^{99m}$Technetium-pertechnetate proximal to the "heart" or input chamber, which was a 132 ml lucite cylinder with an internal diameter and length of 4.34 and 8.9 cm respectively. The "organ" chambers consisted of a large or left "kidney", a 26 ml cylindrical bottle with a diameter and length of 2.9 cm and 4.4 cm respectively, and a small or right "kidney", a 13 ml cylindrical lucite chamber with a diameter and length each 2.5 cm. A "liver" compartment which was not imaged in the current studies contained 1.8 l of fluid. Calibrated electromagnetic flow probes (Carolina Instrument, King, North Carolina) were positioned proximal to the "heart" and distal to each "kidney" to measure "cardiac output" and flow to each "kidney." These flow rates were independently adjustable with "kidney" flow rates ranging from 1.58 to 8.50 ml/sec while "cardiac output" ranged from 30 to 70 ml/sec. Total phantom volume was 2.4±0.1 liters.

System Calibration

A large-field gamma camera (Maxi 535, General Electric, Milwaukee, Wis.) was used with a 20% energy window and a general purpose collimator. The camera was calibrated by acquiring a static study of one phantom kidney filled with known activity, to give the calibration constant $F_G$ in mCi.sec/counts.organ. Dynamic organ curves (counts/sec) $A_1(t)$ and $A_2(t)$ obtained by the gamma camera were multiplied by $F_G$ to give total organ absolute activity (mCi/organ).

The well-counter factor $F_W$ was used to multiply the "heart" or input curve $B(t)$, and thereby convert its dimensions from counts/sec to mCi/ml. $F_W$ was determined by using a known volume of an equilibrium "blood" sample collected at the end of each experiment and its activity determined in a well-counter.

The phantom was filled with saline prior to each experiment. The pump was run for five minutes to stabilize flows after which the electromagnetic flow probes were directly calibrated by timed volumetric measurements.

Data Acquisition

Figure 2:
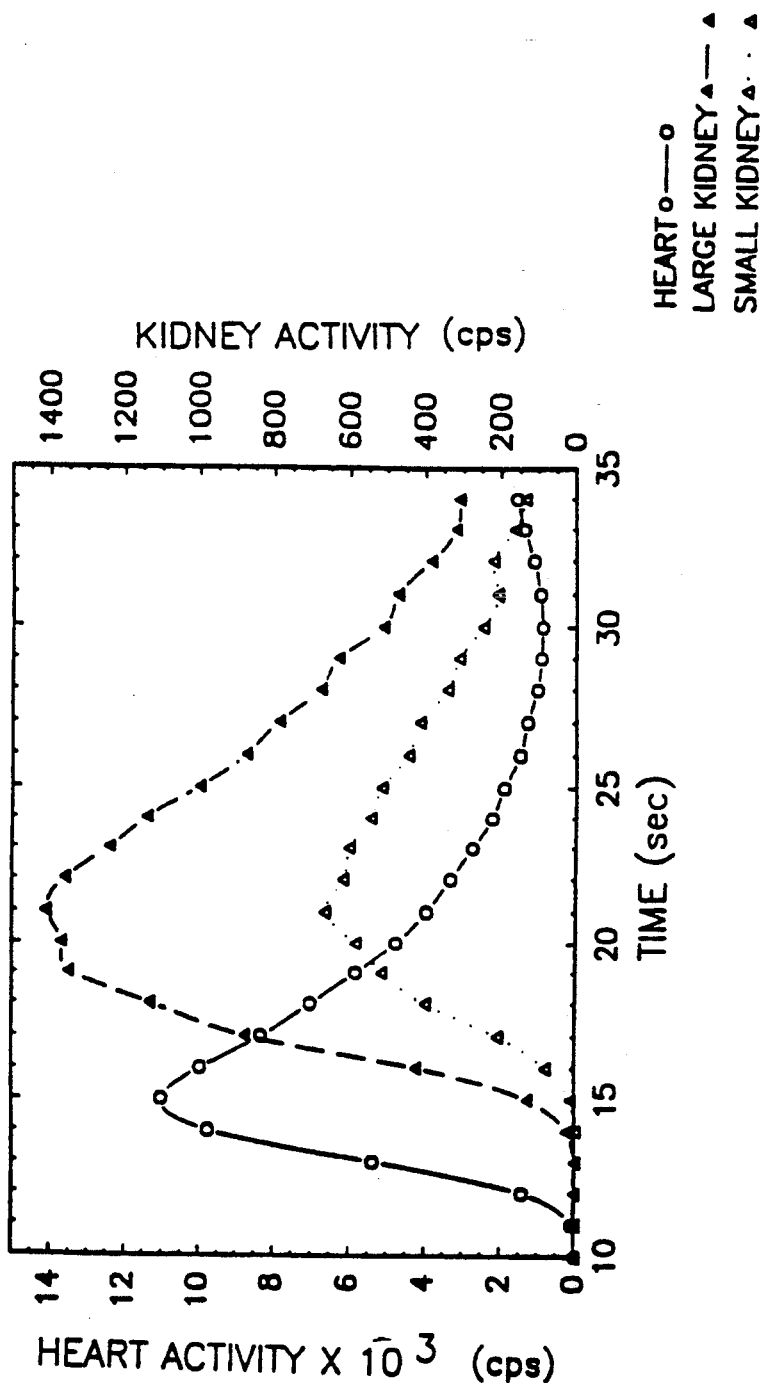
FIG. 2 depicts scintigraphic data showing three time activity curves, in one experiment.

The input ("heart") and both output ("kidney") compartments of the phantom were positioned within the field of view of the gamma camera (FIG. 2). FIG. 2 shows the first curve is the activity recorded from the cardiac chamber (open circles) and the other two curves are the recorded activities from each kidney. The small kidney record is shown as open triangles, while the large kidney record is illustrated with closed triangles. The acquisition of data was commenced a few seconds before the rapid injection of a bolus of $^{99m}$Technetium-pertechnetate of known activity via the injection port. Using the MicroDelta system (Siemens Medical Systems, Des Plains, Ill.), data were recorded at 1 second intervals. Rectangular regions of interest (ROI's) were then defined over the three organs yielding three dynamic time-activity curves, the input curve $B(t)$, and the outut curves $A_1(t)$ and $A_2(t)$. These data, including the calibration factors were then stored on a VAX 11/750 computer (Digital Equipment Company, Maynard, Mass.). FIG. 3 depicts the results of the deconvolution of the data shown in FIG. 2. Symbols used are the same as in FIG. 2.

Data Analysis

The data analysis commences with deconvolution of the input and organ time activity curves to obtain the response of the organ to a perfect impulse bolus input (the LRF). Mathematically, the output $A(t)$ of a linear, stationary system is simply related to its input $B(t)$ by equation (1):

$$A(t) = \int_0^t h(t - t') \cdot B(t') \cdot dt'. \tag{1}$$

the convolution integral, often denoted $A = h*B$, where $h(t-t')$ is the LRF, and * means convolution. In each of the 30 estimations of h(t) by deconvolution (15 experiments with 2 output curves each), the calculation was performed using DOP with a function-space basis of the first 25 Chebycheff polynomials.

Figure 4:
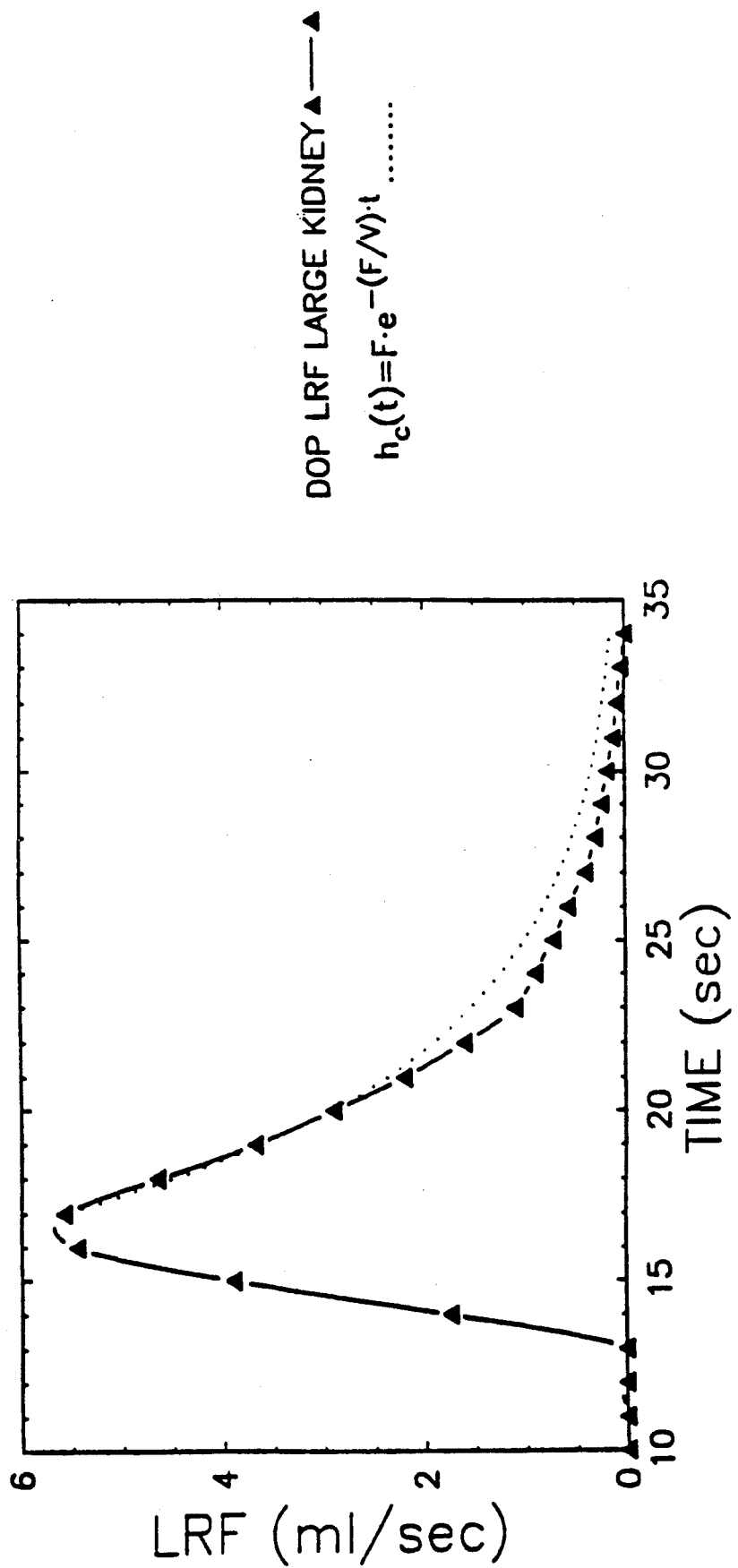
FIG. 4 depicts DOP LRF of a kidney.

The LRF obtained from the circulatory phantom data, was analyzed to determine the organ's perfusion rate. This is achieved by estimating the flow rate from the LRF obtained by DOP, and by tracer kinetics modeling, as described above. These values can then be compared to the values obtained simultaneously by the electromagnetic flow probes. The results confirmed the notion that the LRF contains all kinetic information which characterizes how the organ handles the tracer. The LRFs obtained from direct deconvolution were fitted to a monoexponential decay function of the compartment model as described in equation (D)

$$h_c(t) = Fe^{-(F/V) \cdot t} \tag{D}$$

where $h_c(t)$ is the compartment model LRF, F is the vascular flow rate to the organ, and V is the organ's distribution volume of the tracer. Note that $h_c(t)$ has dimensions of flow in volume per unit time. FIG. 4 shows the results of the same experiment illustrated in FIG. 3 as a solid line and closed triangles. The calculated values for $h_c(t)$ reveal excellent agreement with a monoexponential decay function which is shown as the superimposed dotted line.

Determination of flow rates

LRF Peak Method

Figure 5:
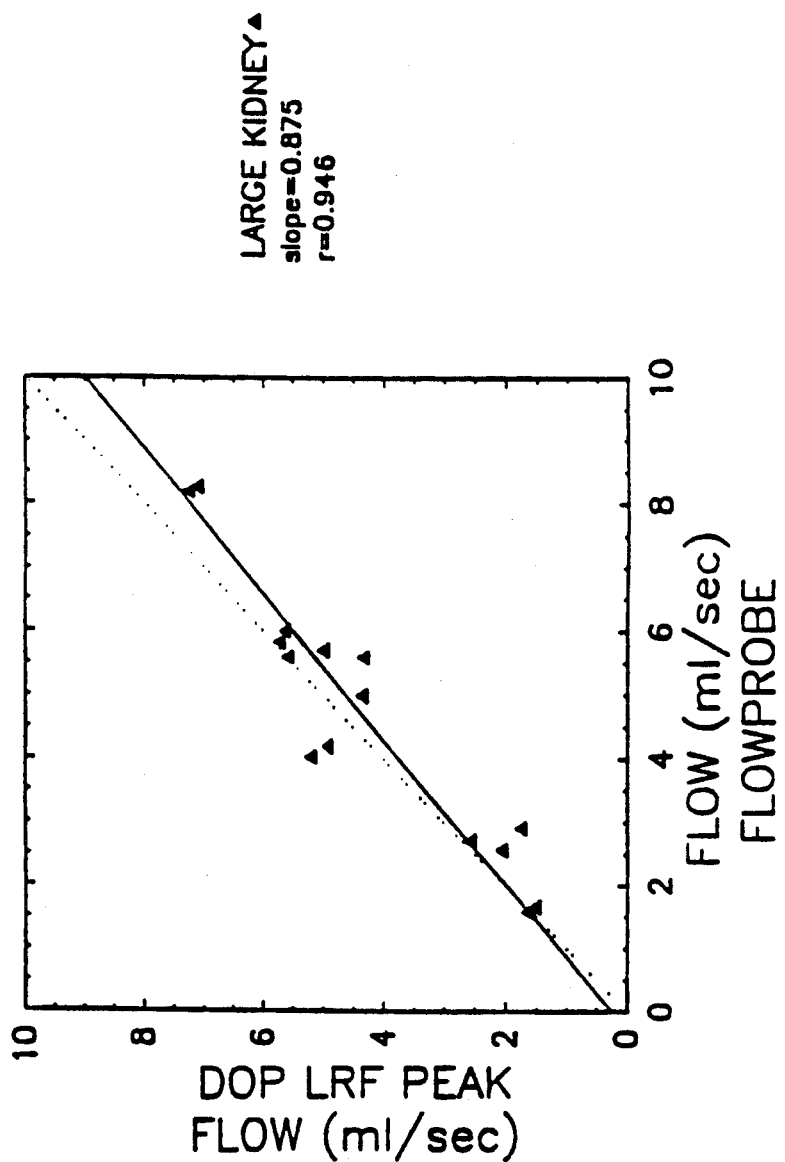
FIG. 5 depicts DOP peak LRF values for large (left) kidney flows compared with rates measured simultaneously by calibrated flow probe. Closed triangles are used for all large kidney graphs.

According to the compartment model, the maximum or peak value of the directly calculated LRF approximates the true flow rate in terms of the maximal value obtained from the compartmental LRF by setting $t=0$ in equation D. To test the hypothesis that the peak value of the DOP LRF provides reliable values for perfusion rates the LRF peak value of flow was compared to that measured directly and simultaneously by the calibrated electromagnetic flow probes (FIG. 5). The calculated value was found to directly correspond to the measured value.

Slope Method for Flow Rate

Figure 6:
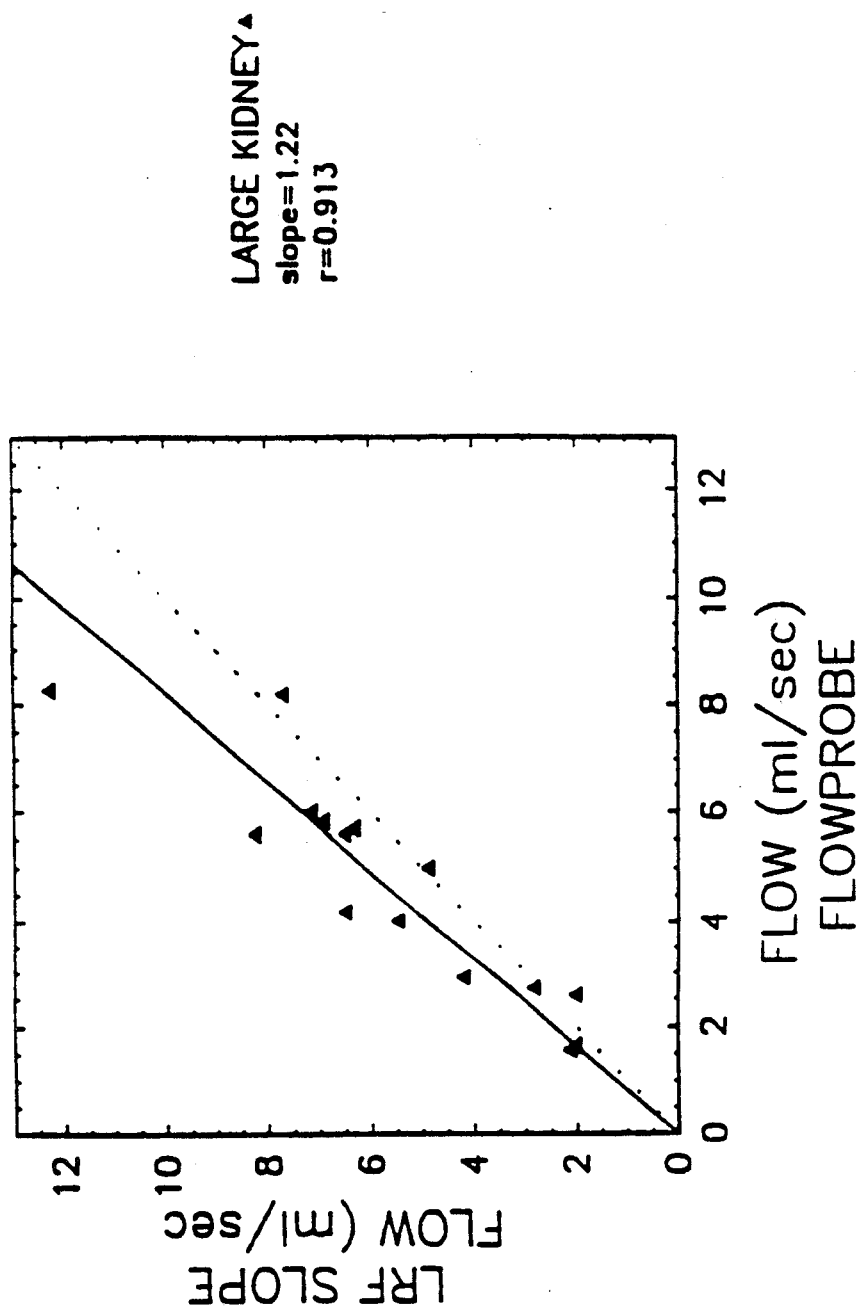
FIG. 6 compares the derived flow rates to the large (left) kidney calculated from the LRF decay constant with those measured simultaneously by calibrated flow-probe.

Our hypothesis that the directly measured DOP LRF contains all kinetic information is proven by showing that the post-peak decay values of the LRF were found to reflect portions of the assumed compartment model. It was found that the decay constant of the LRF equals the ratio of F/V according to equation (D). The slope of the values of ln h(t) derived from the measured LRF was obtained by linear regression for all values of $t \geq t_{peak} + 1$ sec. Since V is known for the phantom, as indicated above, a value for flow, F, may be obtained from the relationship, $F = (slope)(V)$. This value was then compared with that measured directly and simultaneously by the calibrated electromagnetic flow probes. It is clear that in experimental and clinical in vivo settings, the value for the volume of distribution of the organ or system, V, is not known. The results are illustrated in FIG. 6 and substantiate our hypothesis that the DOP LRF contains all relevant kinetic information.

Transit Time Method

A computer program was written to calculate the tracer mean transit time, $\bar{t}$ t, according to equation (E)

$$\bar{t} = \int_0^t t \cdot h_c \cdot dt / \int_0^t h_c \cdot dt. \tag{E}$$

Figure 7:
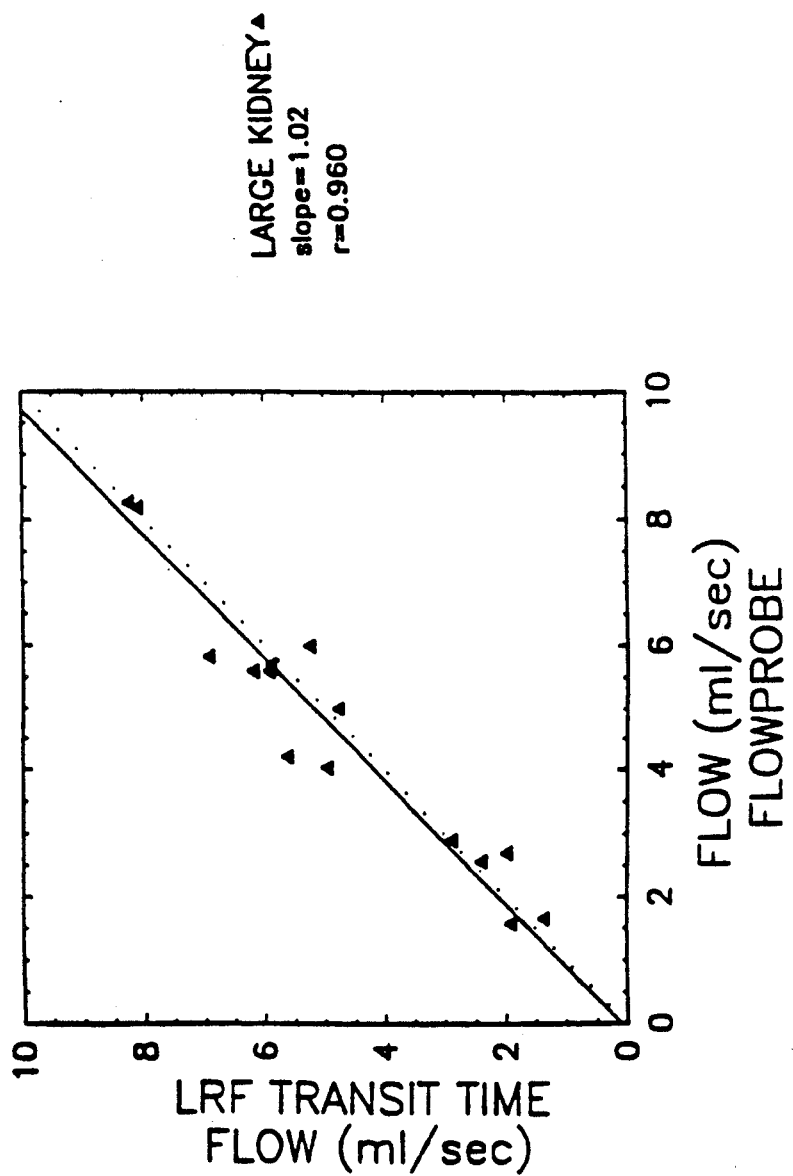
FIG. 7 compares the derived flow rates to the large (left) kidney calculated from the LRF mean transit time with those measured simultaneously by calibrated flow-probe.

Since the value of V is known for the phantom, and F=V/t, a value for F can be derived by dividing V by $\bar{t}$. This value was then compared with that measured directly and simultaneously by the calibrated electromagnetic flow probes. The results are illustrated in FIG. 7 and prove our hypothesis that the DOP LRF contains all relevant kinetic information.

EXAMPLE 2

Clinical data acquisition

The acquisition mode of the dynamic scintigraphic study and the determination of the input function depends on the tracer used and the organ to be investigated. Data acquisition and processing of the input function are described in this example. The measuring system was a gamma camera positioned over the thyroid of the patient and images were recorded in: 5 sec intervals for 100 sec; 10 sec intervals for 2 min; 20 sec intervals for 1 min; 1 min intervals for 4 min; and 2 min intervals for 18 min. Since simultaneous images of the heart and thyroid could not be recorded with the gamma camera available, an external scintillation detector was placed over the heart of the patient. The counts recorded by the scintillation detector were automatically written into one corner of the images. This was accomplished by a electronic switch and buffer system linking the gamma camera and the computer. Each counting event passing by the pulse height analyzer of the probe caused an x,y signal fitting in one of the corners of the gamma camera image. In order to prevent counting overflow, the coordinates were shifted sequentially pixel by pixel by stepwise electronic offset addition $\Delta x$, $\Delta y$ to the x and y position. The size of the total area was an 8 by 8 matrix.

Figure 10:
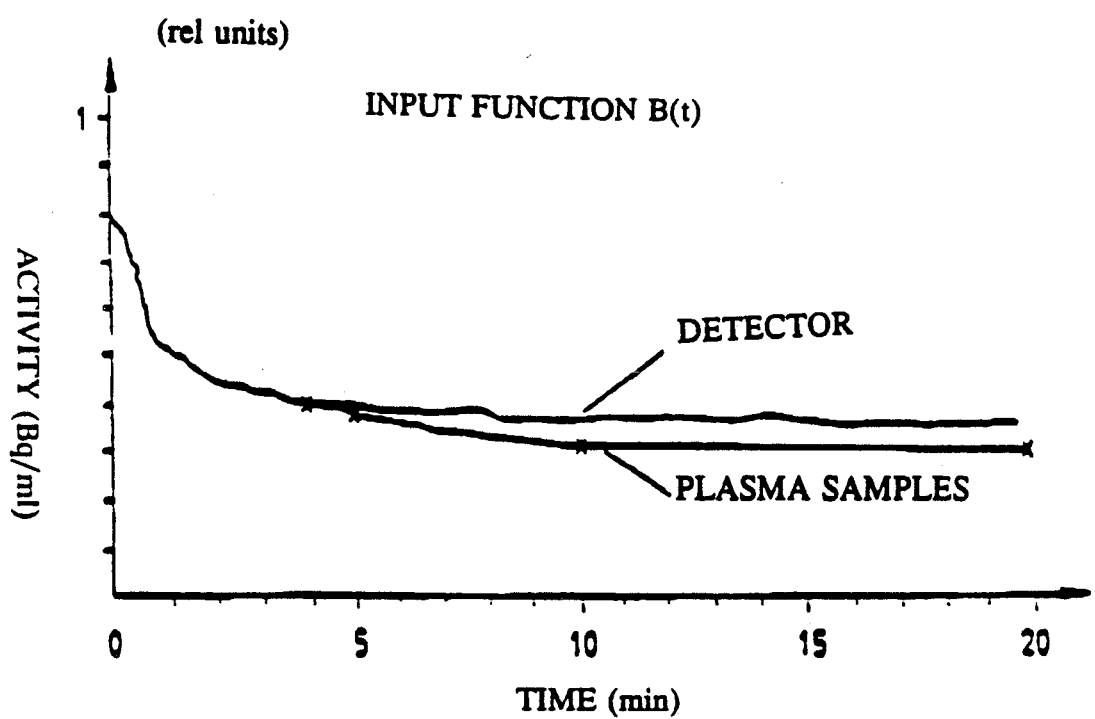
FIG. 10 depicts a detector curve obtained by placing a scintillation detector over the heart to count the time activity course of the tracer in the blood pool.

Simultaneously with acquisition, blood samples were drawn at 3.5, 5, 10 and 20 min after injection. The images acquired during the scintigraphic study were then interpolated, and the input function generated by drawing a region of interest over the $8 \times 8$ matrix. The input function recorded over the heart region mainly reflects the tracer's time course in the blood. Since $^{123}$I is diffusible, the recorded data include activity deriving from intervening extracardiac tissue such as muscle, subcutaneous tissue, etc. This is shown as the upper curve in FIG. 10. As shown in FIG. 10, blood samples Were obtained 3.5, 5, 10 and 20 min after injection, and the tracer activity calculated in 0.5-1 ml blood.

The discrete blood values were interpolated by an exponential fit, and the blood value at 5 min was used to normalize the detector curve at this time point. Detector values at times greater than 5 min were then replaced by values obtained from the interpolated blood curve. This procedure corrected the detector curve for nontarget tissue activity and forms the input function B(t) as discussed in equation (B).

In order to overcome the problem of processing such a compound curve, the recorded curve from the cardiac region of interest was first normalized with the 6 min blood value. In a second step, the heart curve for times greater than 6 minutes was replaced by an exponential fit of the blood values through 3.5, 5, 10, 20 minutes. The resulting curve, shown as the lower curve in FIG. 10, represents data describing the normalized, and corrected input function B(t). The scintigraphic images provide the data which are normalized and converted to the output function A(t) by means of the gamma camera calibration factor $F_G$ described above. From these input and output functions, the LRF was derived as described above in each pixel as a function of time.

Figure 9:
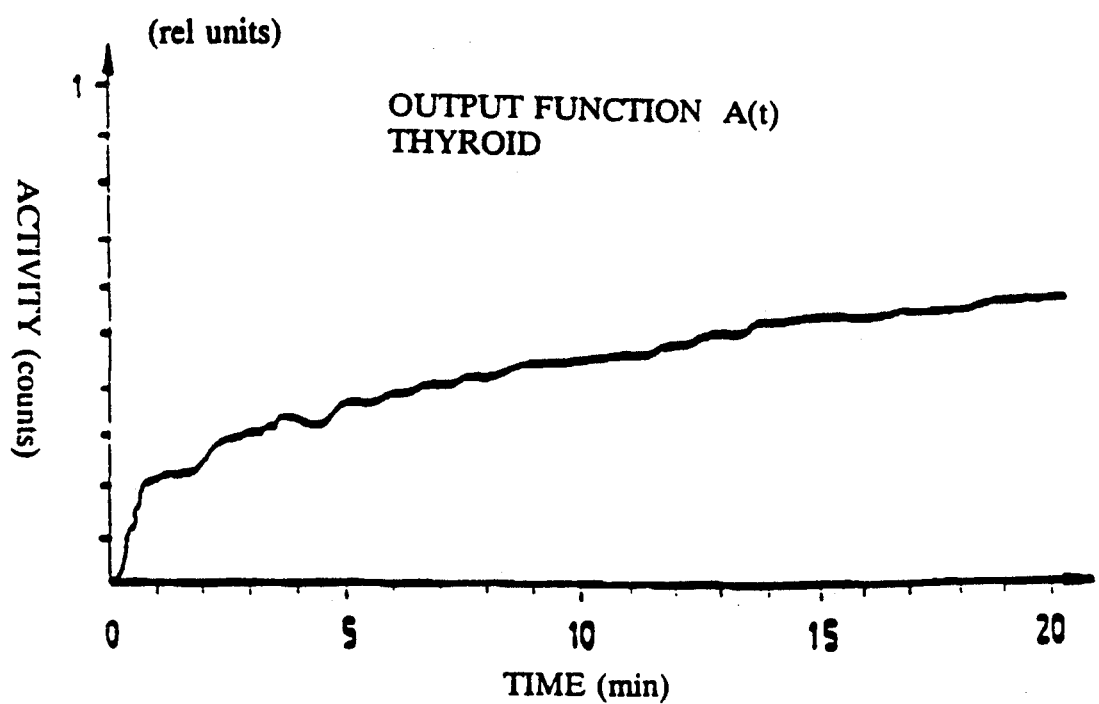
FIG. 9 shows a time activity curve over a region of interest of the thyroid illustrated in FIG. 8 (output function).

An example of the results is shown in FIG. 8. Typical scintigraphic images from a dynamic $^{123}$I thyroid study as described above are shown. The gray scale has been adjusted in each image to encompass exactly the same range of count rates, to enable visual comparison of these images with the results from the deconvolution process. In FIG. 9, the time activity curve from a ROI drawn over the entire thyroid is shown. This curve portrays the accumulation of the tracer into the thyroid. The upper curve in FIG. 10 served as a first order approximation of the input function. This curve was then corrected and normalized by blood samples taken during the scintigraphic acquisition (see FIG. 10 lower curve).

In FIG. 11, images of the LRF calculated from the organ and blood activity (input-output events) are shown. As shown in FIG. 11, the gray scale was arbitrarily adjusted in each image to span a qualitative comparison of the images by visual inspection, which reflect increasing values at the first points, reach a maximum, decrease quickly, and then remain nearly constant (or decrease with a relatively small time constant). The 8 images are a subset of the total of 60 images which were created and represent the first 6 minutes of the tracer kinetics.

In order to compare the functional images, the LRF with the scintigraphic images, the gray scale has been adjusted in each image here as before. The LRF images show the response to a delta functional input of the tracer into the blood and, because no recirculation of the tracer in the blood is allowed, the dependence of the LRF on the kidneys or other organs was thus eliminated. This can be visualized by looking at the LRF images (FIG. 11) and at the time course of the LRF values in the entire thyroid (FIG. 12). The image and curve values commence with low values, rapidly reach a maximum, followed by a rapid and then a slower oscillating decline. This initial response leading to the peak value represents the rapid transfer of the tracer from the blood compartment to both thyroid and nonthyroid tissue spaces. The rapid decline from the peak is due to a rapid outflow of some of the tracer from the thyroid. The example illustrates a physiologically abnormal subject where some of the trapped $^{123}$I is being released rather than being retained and organified. If all of the trapped $^{123}$I were retained, the rate constant would be zero and the LRF would show a constant plateau for $0 \leq t \leq T$, where t denotes the time, and T=25 min is the duration of the study.

EXAMPLE 3

Model patient format

Figure 13A:
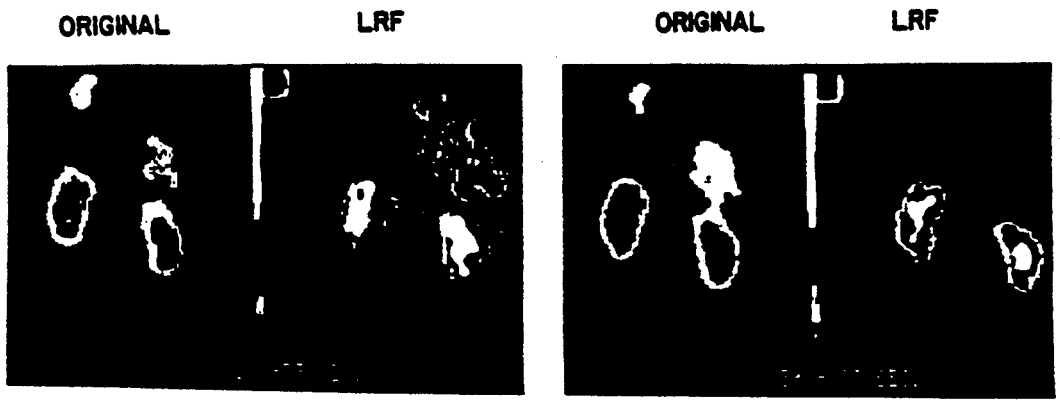
FIG. 13 compares, at identical points in time, side by side, the original dynamic renal $^{123}$I-hippuran scintigrams (prior art) on the left and the created functional images of the kidney on the right.
Figure 13B:
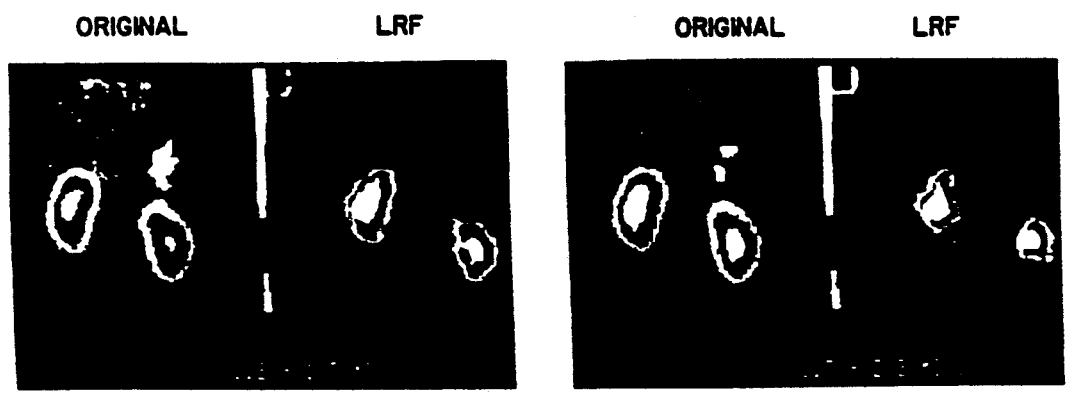
Figure 13C:
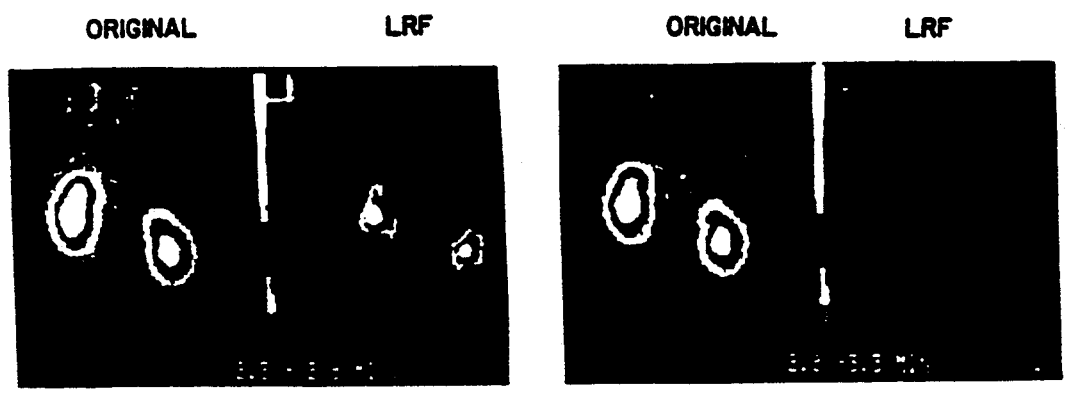

To define the characteristics of renal functional images in patients, it is necessary to obtain images from subjects using either a standard $^{123}$I-hippuran (dose 1-2 mCi) or $^{99m}$Tc-DTPA (dose 10-15 mCi) renogram. Subjects are ambulatory, post-absorptive, and hydrated. The bladder is spontaneously emptied and the time recorded. An indwelling intracath is positioned into a vein in each antecubital fossa, one for the administration of the isotope and the other for collecting a blood sample or samples at known times early after the isotope injection. Starting with the isotope injection, a dynamic scintigraphic study is recorded, 1 sec/image×60 and then 10 sec/image for the next 19 minutes. The bladder is emptied spontaneously immediately after the study and the time and urine volume recorded. Urine is obtained to determine the rate of passage of the tracer from the kidneys to the bladder. Following the procedure outlined above, the results from one patient are illustrated in FIG. 13 which compares, at identical points in time, standard dynamic renal $^{123}$I-hippuran scintigrams (on the left) to functional images of the kidney created by method of the present invention (on the right).

Results of the DOP technique for measuring renal glomerular filtration rate (GFR) using $^{99m}$Tc-DTPA are tabulated in Table 1. These results have been compared with those using creatinine clearance, the standard classical clinical technique for measuring GFR. Both creatinine and $^{99m}$Tc-DTPA are used to measure GFR by determining their rates of clearance by the kidney. The GFR-DOP value can be determined from the plateau of the LRF very quickly, in a matter of minutes. Creatinine is measured by chemical analysis (alkaline Jaffe reaction) in samples of the subject's blood and urine which have been collected during a known timed interval. This chemical analysis is time consuming, in addition, it depends on the accurate collection of timed specimens of urine. Such collection is time consuming if not extremely difficult or impossible without catheterizing the subject. This latter procedure presents additional risk to the subject.

Table 1 shows the GFR determined concurrently by both methods. The GFR-DOP value was determined from the plateau of the LRF. The values of the GFR shown for Patient 1, were determined on different days after renal transplantation (a and b) and show improvement during the interval. Patient 2 was about 2 years post-transplant and shows normal renal function. The use of GFR-DOP is thus faster, less hazardous and at least as accurate as the standard clinical method.

TABLE 1

|  | GFR-Cer (ml/min) | GFR-DOP (ml/min) |
|---|---|---|
| Patient 1 | | |
| (a) | 16 | 20, 20 |
| (b) | 36 | 38 |
| Patient 2 | 107 | 107 |

We claim:

1. A noninvasive method of determining a linear response function of a target organ of a subject selected from the group consisting of animals including man comprising the steps of:
   (a) introducing into the subject's circulatory system a tracer suitable for use in medical imaging;
   (b) obtaining a calibration factor $F_G$;
   (c) obtaining a plurality of time sequenced measurements of the counts per unit time of the tracer in the target organ with a measuring system capable of monitoring the tracer;
   (d) multiplying the measurement obtained in step (c) by $F_G$ to obtain a corrected measured absolute activity per volume, output function A(t);
   (e) obtaining with a measuring system capable of monitoring the tracer, concurrently with step (c), a plurality of time sequenced measurements of the tracer within the subject's heart or great vessels;
   (f) withdrawing from the subject one blood sample after the tracer injection at time $t_1$;
   (g) normalizing timewise the measured tracer in the heart or great vessels with respect to the value at time $t_1$;
   (h) measuring the amount of the tracer in the blood sample with a measuring system capable of monitoring the tracer;
   (i) converting the measured tracer in the blood sample as absolute tracer activity/volume by means of a calibration factor $F_w$ computed from (g) and (h) above;
   (j) multiplying the activity obtained in step (g) by $F_w$ to obtain an input function B(t); and
   (k) deconvolving the combination of A(t) and B(t) thereby deriving h(t), the linear response function of the target organ.

2. The method according to claim 1 wherein the measuring system calibration comprises the steps of:
   (a) obtaining a measurement, with a measuring system capable of monitoring the tracer, of a sample of tracer having a known volume and a known activity under conditions simulating an in vivo situation; and
   (b) multiplying the measurement obtained in step (a) by the known activity of the tracer to obtain a correction factor $F_G$.

3. The method according to claim 1 wherein the measuring systems are selected from the group consisting of scintillation detectors, gamma cameras, single photon emission tomography, position emission tomography, nuclear magnetic resonance imaging and digital subtraction radiography.

4. The method according to claim 1 further comprising the step of creating functional images of the target organ at any stages of its linear response function in still and cine mode pictures.

5. A noninvasive method of determining a linear response function of a target organ of a subject selected from the group consisting of animals including man comprising the steps of:
   (a) introducing into the subject's circulatory system a tracer suitable for use in medical imaging;
   (b) obtaining a calibration factor $F_G$;
   (c) obtaining a plurality of time sequenced measurements of the counts per unit time of the tracer in the target organ with a measuring system capable of monitoring the tracer;
   (d) multiplying the measurement obtained in step (c) by $F_G$ to obtain a corrected measured absolute activity per volume, output function A(t);
   (e) obtaining with a measuring system capable of monitoring the tracer, concurrently with step (c), a plurality of time sequenced measurements of the tracer within the subject's heart or great vessels;
   (f) withdrawing from the subject one blood sample after the tracer injection at time $t_1$;
   (g) normalizing timewise the measured tracer in the heart or great vessels with respect to the value at time $t_1$;
   (h) measuring the amount of the tracer in the blood sample with a measuring system capable of monitoring the tracer;
   (i) converting the measured tracer in the blood sample as absolute tracer activity/volume by means of a calibration factor $F_w$ computed from (g) and (h) above;

(j) multiplying the activity obtained in step (g) by $F_w$ to obtain an input function B(t);

(k) digitizing A(t) and B(t);

(l) identifying a first plurality of orthonormal functions $c_z$ derived from B(t);

(m) identifying a second plurality of orthonormal functions $d_z$ having the same number of elements as function $c_z$;

(n) applying second plurality of functions $d_z$ to calculate a set of values $f_z$ from the product of the elements of $d_z$ and the values of A(t);

(o) calculating the linear response function of the target organ h(t) from the sum of the products of each individual elements of $c_z$ and $f_z$.

6. The method according to claim 5 wherein the measuring system calibration comprises the steps of:

(a) obtaining a measurement, with a measuring system capable of monitoring the tracer, of a sample of tracer having a known volume and a known activity under conditions simulating an in vivo situation; and (b) multiplying the measurement obtained in step (a) by the known activity of the tracer to obtain a correction factor $F_G$.

7. The method according to claim 5 wherein the measuring systems are selected from the group consisting of scintillation detectors, gamma cameras, single photon emission tomography, position emission tomography, nuclear magnetic resonance imaging and digital subtraction radiography.

8. The method according to claim 5 further comprising the step of creating functional images of the target organ at any stages of its linear response function in still and cine mode pictures.

9. A noninvasive method of determining a linear response function of a target organ of a subject selected from the group consisting of animals including man comprising the steps of:

(a) introducing into the subject's circulatory system a tracer suitable for use in medical imaging;

(b) obtaining a calibration factor $F_G$;

(c) obtaining a plurality of time sequenced measurements of the counts per unit time of the tracer in the target organ with a measuring system capable of monitoring the tracer;

(d) multiplying the measurement obtained in step (c) by $F_G$ to obtain a corrected measured absolute activity per volume, output function A(t);

(e) obtaining with a measuring system capable of monitoring the tracer, concurrently with step (c), a plurality of time sequenced measurements of the tracer within the subject's heart or great vessels;

(f) withdrawing from the subject one blood sample after the tracer injection at time $t_1$;

(g) normalizing timewise the measured tracer in the heart or great vessels with respect to the value at time $t_1$;

(h) measuring the amount of the tracer in the blood sample with a measuring system capable of monitoring the tracer;

(i) converting the measured tracer in the blood sample as absolute tracer activity/volume by means of a calibration factor $F_w$ computed from (g) and (h) above;

(j) multiplying the activity obtained in step (g) by $F_w$ to obtain an input function B(t);

(k) digitizing A(t) and B(t) and organizing them into two separate two dimensional images, each image having pixels containing the amplitude of A(t) and B(t) respectively;

(l) computing a first plurality of orthonormal functions, each of said first functions having a plurality of first elements;

(m) computing a second plurality of orthonormal functions, each of said second functions having a plurality of second elements;

(n) computing a first product for each pixel element contained in said sequence of images of A(t), said first product computed from each second element of said second plurality of orthonormal function and pixels from said images of A(t);

(o) computing sum of a second product, said second product computed from each first element of said first plurality of orthonormal functions and each element of said first product.

* * * * *

UNITED STATES PATENT AND TRADEMARK OFFICE
CERTIFICATE OF CORRECTION

PATENT NO. : 5,287,273

DATED : February 15, 1994

INVENTOR(S) : Sherman Kupfer and Peter Stritzke

It is certified that error appears in the above-indentified patent and that said Letters Patent is hereby corrected as shown below:

Title page, Page 2, 1st col., penultimate line, "367 α 388" should read --367-388--.

Title page, Item 56, line 4, "(1985)" should read --(1965).

Title page, Item 56, line 6, after "154" insert --(1967)--.

Title page, Item 56, line 9, after "863" insert --(1988)--.

Title 3, 1st col., 2nd line, "(RFB)" should read --(RBF)--.

Col. 3, 1st col., bridging lines 16-17, "Rubidinum-82" should read --Rubidium-82--.

Col. 9, line 8, "(o)" should read --(°)--.

Col. 9, line 58, that portion of equation (12) reading "$(x,y,t_n+1°)$" should read --$(x,y,t_n^°+1)$ Col. 11, line 10, that portion of equation (17d) reading "$a_{31}$" should read --$a_{41}$--.

Col. 11, line 57, that portion of equation (19a) reading "$b_1|b_2$" should read --$b_1|b_1$--.

Col. 12, line 67, "Introductor" should read --Introductory--.

Col. 15, line 7, ">k|" should read --<k|--.

Col. 21, line 50, "Were" should read --were--.

UNITED STATES PATENT AND TRADEMARK OFFICE
CERTIFICATE OF CORRECTION

PATENT NO. : 5,287,273

DATED : February 15, 1994

INVENTOR(S) : Sherman Kupfer and Peter Stritzke

It is certified that error appears in the above-indentified patent and that said Letters Patent is hereby corrected as shown below:

Col. 25, line 16, "elements" should read --element--.

Signed and Sealed this

Fourteenth Day of February, 1995

Attest:

BRUCE LEHMAN

*Attesting Officer*     *Commissioner of Patents and Trademarks*